(12) United States Patent
Maxwell

(10) Patent No.: US 9,605,279 B2
(45) Date of Patent: Mar. 28, 2017

(54) METHODS AND SYSTEM FOR PHOTO-ACTIVATED HYDROGEN GENERATION

(71) Applicant: BOMAX Hydrogen LLC, Orlando, FL (US)

(72) Inventor: Deborah B. Maxwell, DeLand, FL (US)

(73) Assignee: BOMAX Hydrogen LLC, Orlando, FL (US)

( * ) Notice: Subject to any disclaimer, the term of this patent is extended or adjusted under 35 U.S.C. 154(b) by 120 days.

(21) Appl. No.: 14/620,386

(22) Filed: Feb. 12, 2015

(65) Prior Publication Data

US 2015/0225742 A1    Aug. 13, 2015

Related U.S. Application Data

(60) Provisional application No. 61/939,430, filed on Feb. 13, 2014.

(51) Int. Cl.
| | | |
|---|---|---|
| *C12P 3/00* | (2006.01) | |
| *B82Y 5/00* | (2011.01) | |
| *C12N 9/02* | (2006.01) | |
| *C07K 14/195* | (2006.01) | |

(52) U.S. Cl.
CPC  *C12P 3/00* (2013.01); *B82Y 5/00* (2013.01); *C07K 14/195* (2013.01); *C12N 9/0095* (2013.01); *C12Y 118/06001* (2013.01)

(58) Field of Classification Search
CPC  C12P 3/00; B82Y 5/00; C07K 14/195; C12N 9/0095; C12Y 118/6001
See application file for complete search history.

(56) References Cited

PUBLICATIONS

Maxwell, "Iron-Molybdenum Cofactor: Catalyst in Dihydrogen Production and Role of Nifen in the FeMo—Co Biosynthetic Pathway." Dissertation, University of Central Florida 1-109, 2012.
Rubio et al., "Purification and Characterization of NafY (Apodinitrogenase [gamma] Subunit) from Azotobacter vinelandii." Journal of Biological Chemistry 279(19): 19739-19746, 2004.
International Search Report mailed on May 14, 2015 for PCT/US2015/015560.

*Primary Examiner* — Susan Hanley
(74) *Attorney, Agent, or Firm* — Greenberg Traurig, LLP; Fang Xie; Joshua R. Brown

(57) ABSTRACT

Systems and methods for providing alternative fuel, in particular hydrogen photocatalytically generated by a system comprising photoactive nanoparticles and a nitrogenase cofactor are provided. In one aspect, the system includes a water soluble cadmium selenide nanoparticle (CdSe) surface capped with mercaptosuccinate (CdSe-MSA); and a NafY.FeMo-co complex comprising a NafY protein and an iron-molybdenum cofactor (FeMo-co); wherein the CdSe-MSA and the NafY.FeMo-co complex are present in about 1:1 molar ratio in a CdSe-MSA.NafY.FeMo-co system. In various embodiments, when illuminated, the CdSe-MSA.NafY-.FeMo-co system is capable of photocatalytically producing hydrogen gas for an extended period of, e.g., at least 5 hours, at least 10 hours, or at least 90 hours. Methods for making and using the same are also provided.

23 Claims, 14 Drawing Sheets

METHODS AND SYSTEM FOR PHOTO-ACTIVATED HYDROGEN GENERATION

CROSS-REFERENCE TO RELATED APPLICATIONS

This application claims the benefit of and priority to U.S. Provisional Application No. 61/939,430 filed Feb. 13, 2014, the entire disclosure of which is incorporated herein by reference.

TECHNICAL FIELD

The present disclosure relates in general to systems and methods for providing alternative fuel, in particular hydrogen photocatalytically generated by a system comprising photoactive nanoparticles and a nitrogenase cofactor.

BACKGROUND

With trade and commerce of energy resources and ecological threats stemming from their use impacting geopolitical stability, the reality is that humankind is at a crossroads, which in turn is driving an imperative to develop alternative energy sources. Humankind's tremendous industrial and technological progress over the last two centuries has been driven by the natural abundance and availability of fossil fuels. As those reserves deplete, the prudent course of action would be to develop other readily available fuel sources. Currently, 15 terawatts ($1.5\times10^{13}$ Watts) of energy are consumed worldwide annually, with fossil fuels providing 86% of that energy. The categories of energy forms used each year are 40% petroleum, 23% natural gas, 23% coal, 8% nuclear, and 6% from renewable sources. The projected years left in reserves at the current usage levels are estimated at 47 years for petroleum reserves, 60 years for natural gas reserves and 131 years for coal reserves [1].

Renewable energy sources include solar, wind, hydroelectric and geothermal options. Solar energy is accessed and utilized in several ways. An important way is the use of silicon based solar cells that produces electric current. A recent important breakthrough in the research of inexpensive materials for energy applications is the use of a silicon sheet coated with a cobalt based catalyst on one side and a nickel-molybdenum-zinc alloy layer on the opposite side [2]. This device, named the artificial leaf, produces notable amounts of hydrogen and oxygen when submerged in water and illuminated. Another major current research effort involves the use of $TiO_2$ exposed to UV radiation which splits water into hydrogen and oxygen [3]. Water-splitting $TiO_2$ is mostly used in fuel cells that generate electric current from the oxidation of hydrogen. The challenge over the last three decades has been to develop novel materials to perform water splitting with energy from the visible light region of the electro-magnetic spectrum. The use of nanoparticles alone or in composite materials with $TiO_2$ show promise for improving this exploitation of solar energy [4].

Another research area toward the goal of accessing solar energy, but with a somewhat different outcome is the production of hydrogen as an alternative fuel source by utilizing biomolecules. Some researchers using biological systems to produce hydrogen, utilize one or both of two enzymes of hydrogenases and nitrogenases found in certain microorganisms. Developing ways to utilize and adapt this hydrogen generating ability of these enzyme systems can be grouped in three broad approaches: using an enzyme itself; forming a hybrid between different enzyme components and a synthetic material, or by synthesizing a biomimetic analog of the biological catalyst.

Some research efforts using biomolecules involve the hydrogenases and nitrogenases with the goal of evolving hydrogen. There are several published methods that have photocatalytically generated hydrogen. For example, self-assembled complexes between cadmium telluride nanocrystals and Fe—Fe hydrogenase from *Clostridium acetobutylicum* when illuminated with a visible light source have produced hydrogen with ascorbic acid serving as an electron donor [5]. A NiFeSe-hydrogenase from *Desulfomicrobium baculatum* complexed with ruthenium dye-sensitized $TiO_2$ was illuminated either with a tungsten halogen lamp or with sunlight and was effective for production of hydrogen [6]. An altered molybdenum-iron protein (MoFe protein), component I protein of nitrogenase, was complexed with $Ru(bypy)_2$ near the catalytic site. When the complex was illuminated with a xenon/mercury lamp and provided with the substrates of protons or acetylene, the system produced the corresponding reduced products of hydrogen and ethylene [7].

However, the above systems have only displayed limited capability and efficiency in producing hydrogen ($H_2$). In particular, the longest lasting hydrogen production system utilizing inexpensive nanoparticles complexed to a nitrogenase or hydrogenase in published research to date is only 4 hours. Thus, a need exists for improved systems and methods for producing hydrogen, in particular over an extended or prolonged period of time (e.g., for at least 5 hours, at least 10 hours, at least 50 hours, at least 90 hours, or at least 100 hours, or longer).

SUMMARY

Systems and methods for photocataytically producing hydrogen gas passively as an alternative fuel source are provided herein. In one aspect, a CdSe.NafY.FeMo-co system has been developed, wherein cadmium selenide nanoparticles are complexed with NafY protein containing iron-molybdenum cofactor, FeMo-co, from nitrogenase. Interrogation of the CdSe.NafY.FeMo-co system by electron paramagnectic spectroscopy (EPR) suggested electron transfer events from FeMo-co. When the system is illuminated with visible light hydrogen gas can be evolved. The CdSe.NafY.FeMo-co system unexpectedly holds up for a prolonged period of time (e.g., 90 plus hours) while producing hydrogen throughout.

In one aspect, a system for photocatalytically producing hydrogen gas is provided. The system includes a water soluble cadmium selenide nanoparticle (CdSe) surface capped with mercaptosuccinate (CdSe-MSA); and a NafY-.FeMo-co complex comprising a NafY protein and an iron-molybdenum cofactor (FeMo-co). In some embodiments the CdSe-MSA and the NafY.FeMo-co complex are present in about 1:1 molar ratio to form a CdSe-MSA.NafY.FeMo-co system. In various embodiments, when illuminated, the CdSe-MSA.NafY.FeMo-co system is capable of photocatalytically producing hydrogen gas for an extended period of, e.g., at least 5 hours, at least 10 hours, or at least 90 hours.

In some embodiments, the system can be kept under anaerobic conditions and in the presence of a dithionite salt. The dithionite salt can be, e.g., sodium dithionite. In some embodiments, the dithionite salt is kept at a constant concentration of, e.g., 2 mM, which helps continuous and extended hydrogen production by the system. The system can also be kept at a temperature between, e.g., about 30-40° C., about 35° C., or about 40° C., to favor formation of the monomer form of dithionite.

In another aspect, a method of producing hydrogen gas is provided. The method includes illuminating the CdSe-MSA.NafY.FeMo-co system described herein. In some embodiments, the method includes producing hydrogen gas for an extended period of, e.g., at least 5 hours, at least 10 hours, or at least 90 hours. Fuel cells containing the CdSe-MSA.NafY.FeMo-co system described herein are also provided.

In a further aspect, a method for preparing a system for photocatalytically producing hydrogen gas is provided. The method includes: (a) providing a water soluble cadmium selenide nanoparticle (CdSe) surface capped with mercaptosuccinate (CdSe-MSA); (b) providing a NafY.FeMo-co complex comprising a NafY protein and an iron-molybdenum cofactor (FeMo-co); and (c) mixing the CdSe-MSA and the NafY.FeMo-co complex under anaerobic conditions to form a CdSe-MSA.NafY.FeMo-co system, wherein when illuminated, the CdSe-MSA.NafY.FeMo-co system is capable of photocatalytically producing hydrogen gas.

In some embodiments, step (a) further comprises exchanging surface capping agent from trioctylphosphine (TOP) in a CdSe-TOP nanoparticle to mercaptosuccinate, to form the CdSe-MSA. In one embodiment, the CdSe-TOP nanoparticle has a diameter of about 2.4 nm to about 2.7 nm and/or the CdSe-MSA has a diameter of about 2.6 nm. In certain embodiments, the exchanging step is performed in methanol under reflux in the presence of a base such as quaternary ammonium salts. For example, the base can be tetrabutylammonium hydroxide.

In certain embodiments, in step (b), the NafY protein is derived from *Azotobacter vinelandii*(wild type). The FeMo-co can be derived from a molybdenum-iron protein (MoFe protein). In one embodiment, the MoFe protein is derived from *Azotobacter vinelandii* strain DJ995. Step (b) can further include combining the NafY protein with stepwise aliquots of the FeMo-co to form the NafY.FeMo-co complex. For example, the FeMo-co can be provided in N-methylformamide (NMF) solution and added stepwise to the NafY protein so that NMF does not exceed about 3% (v/v).

In some embodiments, in step (c), the CdSe-MSA and the NafY.FeMo-co complex are provided at about 1:1 molar ratio. The CdSe-MSA can be provided in the presence of a dithionite salt. In some embodiments, the dithionite salt can be kept at a sufficiently low concentration so as to allow the CdSe-MSA and the NafY.FeMo-co complex to bind to each other. Thereafter, the dithionite salt concentration can be increased (e.g., by about 5 fold, 10 fold, 20 fold, or higher or lower) to facilitate hydrogen gas production by the CdSe-MSA.NafY.FeMo-co system.

BRIEF DESCRIPTION OF THE DRAWINGS

(FIG. 3A) Fluorescence emission spectra of CdSe-TOP (10 μM) with sequential 1 μL additions of FeMo-co solution (60 μM stock). The plots show a decrease of fluorescence intensity for the CdSe-TOP. (FIG. 3B) Fluorescence spectra of CdSe-TOP with sequential additions of the same volumes of the solvent NMF solution as the FeMo-co additions. The solid black line is the CdSe-TOP before any additions. The first five additions of NMF are shown with dotted lines showing an increased photoluminescence. With the additions of 6-10 μL NMF, the CdSe-TOP fluorescence is progressively quenched. (FIG. 3C) The data in panels A and B are replotted as percent quenching to compare the quenching by FeMo-co (▲) and NMF (●).

(FIG. 6A) NafY protein excited at 280 nm showing progressive fluorescence quenching at 347 nm with additions of CdSe-MSA seen. There is also an emission at 532 nm that increases as more CdSe-MSA is added. (FIG. 6B) Excitation of the same sample at 410 nm. With this emission the second emission in panel A is confirmed to be from the CdSe-MSA. (FIG. 6C) Replot of the data in A shows percent NafY quenching versus CdSe-MSA concentration. The plot shows a saturation type curve indicating the formation of a complex. (FIG. 6D) Replot of the data in FIG. 6B shows increasing photoluminescent intensity with increasing CdSe-MSA concentration.

(FIG. 8A) Absorbance spectra showing time dependent light induced reduction of methyl viologen by CdSe-MSA (0.72 μM). Methyl viologen (1.47 mM) and dithiothreitol (14.7 mM) were added prior to illumination. (FIG. 8B) Replot of data in A shows time dependence increase in reduced methyl viologen absorption at 603 nm (720 nM CdSe-MSA) (black trace) compared to the control sample (green trace). Additionally a concentration dependent absorption of twice the amount of CdSe-MSA is shown (1440 nM) (red trace).

(FIG. 12A) Hydrogen production by a 1:1 CdSe-MSA.NafY.FeMo-co system with illumination over 130 hours in four different experimental sets with the same reaction conditions. (FIG. 12B) Two duplicate samples from within (FIG. 12A) with error bars.

DETAILED DESCRIPTION

Figure 1:
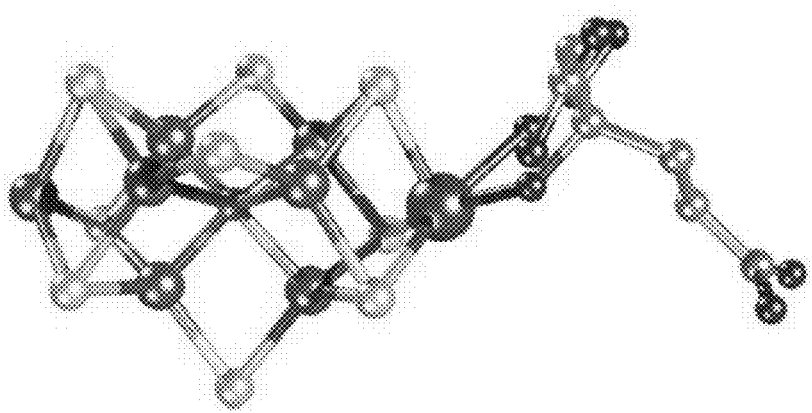
FIG. 1. Structure of the Iron-Molybdenum Cofactor (FeMo-co). The $Fe_7MoS_9C$—(R)-homocitrate cluster is comprised of 7 irons (green), 9 sulfurs (yellow), one carbon (gray), one molybdenum (magenta), and one (R)-homocitrate ligand.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, database entries, and other references mentioned herein are incorporated by reference in their entirety. In case of conflict, the present specification, including definitions, will control.

As used herein, the articles "a" and "an" are used herein to refer to one or to more than one (i.e., to at least one) of the grammatical object of the article. By way of example, "an element" means one element or more than one element.

As used herein, the term "about" means within 20%, more preferably within 10% and most preferably within 5%.

The present disclosure relates to a catalytic system that can harness solar energy and produce an alternative fuel will be the paramount challenge of this new century. Indeed by its end the most widely used fossil fuel, petroleum, may have run dry. Several catalytic systems have been reported in scientific literature that utilizes both natural products and man-made components. Some of the hybrid systems use hydrogenase, an enzyme that both reduces and oxidizes hydrogen in bacteria, either alone or in combination with photosystem I, coupled to platinum. The goal of the present disclosure was to develop a system that would use a smaller catalytic natural component along with a less expensive light harvesting semi-conductor rather than the metal platinum, which is of limited availability. Surprisingly, the system of the present disclosure displays unexpected longevity and can produce hydrogen for a prolonger period of time. Methods for making and using the system are also provided.

CdSe Nanoparticles and FeMo-co

Provided herein is a different approach than conventional methods for photocatalytically generating hydrogen. The systems and methods of the present disclosure, in some embodiments, include cadmium selenide (CdSe) nanoparticles (NPs) which are a photoactive material responsive to light in the visible light spectrum. CdSe NPs, also referred to as quantum dots, can be synthesized by a high temperature pyrolysis with the targeted size of, for example, 2.4 to 2.7 nanometers in diameter. Such nanoparticles demonstrate unique properties compared to bulk sized particles, such as size tunable luminescence. When synthesized they can be dissolved in organic solvents, such as chloroform or octadecence [35].

CdSe NPs have a band gap energy near the thermodynamic potential of hydrogen ion reduction at pH of 7. When CdSe NPs are excited with light energy exceeding their band gap, electrons are promoted from the valence band to the conduction band, generating excitons, electron-hole pairs. If a charge separation can be maintained, the electrons can be available for transfer to an adsorbed species on the nanoparticle surface [3].

In some embodiments, a natural catalytic substance, iron-molybdenum co-factor, FeMo-co, from nitrogenase that reduces hydrogen ions to form hydrogen gas can be introduced to the surface of the cadmium selenide nanoparticle. The use of the natural product hydrogenase was mentioned previously as a component in other alternative fuel research methods. Instead of hydrogenase, however, the choice for a natural catalyst in this disclosure is the iron-molybdenum co-factor in nitrogenase found in diazotrophic bacteria. It is the most studied iron-sulfur cluster of its kind among the nitrogenases. FeMo-co catalyzes the energetically uphill reduction of nitrogen gas, considered inert, to form $NH_3$ and hydrogen as a byproduct, thereby providing the major route by which nitrogen enters the biosphere. It's instructive to compare the work of FeMo-co to Haber-Bosch, a man-made process that requires 200-300 atmospheres of pressure and 300° C. and upwards to accomplish nitrogen fixation. Nitrogenase performs the very same with the aid of FeMo-co in ambient pressure and temperatures.

FeMo-co is shown in FIG. 1, which is the catalytic cofactor found in the active site of the molybdenum-iron protein (MoFe protein) component of nitrogenase. The MoFe protein and Fe protein, also denoted as component I and component II, respectively, are the two proteins that comprise nitrogenase. The Fe protein is a 63 kDa homodimer that has a single $Fe_4S_4$ cluster at the dimer interface. The MoFe protein is a 240 kDa $\alpha_2\beta_2$-heterotetramer with two types of Fe—S clusters, the P-cluster and FeMo-co. The P-cluster, a $Fe_8S_7$ cluster, is at the interface of the α and β subunits of the MoFe protein. At the nitrogenase active site, the iron-molybdenum cofactor (FeMo-co) catalyzes the reduction of nitrogen and protons to form ammonia and hydrogen. FeMo-co is a $Fe_7MoS_9$C-R-homocitrate cluster (FIG. 1) within the active site in the α-subunits. Each FeMo-co is conjugated at the terminal iron by a thiolate of a cysteine ($\alpha$-$275^{Cys}$) and at the other end on the molybdenum by the ε-N of a histidine ($\alpha$-$442^{His}$)[8,9], The-R-homocitrate is coordinated through its C-2 carboxyl and hydroxyl groups to the molybdenum [10]. The Fe-protein binds Mg-ATP, docks to the MoFe protein, hydrolyzes the bound Mg-ATP, and couples the liberated free energy to inter-protein transfer of a single electron to the P-cluster of the MoFe protein (Equation 1). Electrons are then transferred from the P-cluster to FeMo-co where an eight electron reduction of $N_2$ and protons occur producing $NH_3$ and $H_2$ (Equation 1) [11]. In the absence of any substrates, such as nitrogen or acetylene, FeMo-co readily reduces protons to form hydrogen [12, 13].

$$N_2 + 8e^- + 16\ MgATP + 8H^+ \rightarrow 2NH_3 + H_2 + 16MgADP + 16P_i \quad \text{(Equation 1)}$$

The best model in literature, the Thorneley-Lowe mechanism [64], describes how the Fe protein with two bound Mg-ATP binds to MoFe protein, thought to induce a conformational change resulting in lowered activation energy. The two MgATP undergo hydrolysis and one electron is delivered first to the P-cluster and then to FeMo-co. The Fe protein dissociates from the Mo—Fe protein. Each of these electron transfer events are labeled $E_n$, $E_{1-8}$, in the Thorneley-Lowe model and four electrons must interact with FeMo-co before the nitrogen substrate binds. An alternating pathway versus a distal pathway is now favored and proposes that at FeMo-co the two nitrogens bound to Fe are hydrogenated alternately. After four steps, it is believed that a hydrazine intermediate forms and after step five the first $NH_3$ is released. Substrates, NH=NH, and NH=N—$CH_3$ along with trapped intermediates and genetically modified MoFe protein allowed for this selection versus the distal pathway which hypothetically yields different intermediates. The second $NH_3$ is released after $E_8$ step [65]. In the absence of any substrates, such as dinitrogen or acetylene, FeMo-co readily reduces protons to form hydrogen, done so by the formation of hydrides on Fe [66]. When nitrogen and other substrates are absent, yet provided with a source of hydrogen ions, FeMo-co readily reduces $H^+$ to form hydrogen gas [67]. Thus, FeMo-co, one of the most reductive catalysts in nature, is a powerful reductant for the formation of hydrogen gas.

FeMo-co can be prepared by in vitro and/or in vivo methods such as chemical synthesis or recombinant proteins. For example, *Azotobacter vinelandii* cells (wild-type or engineered) can be grown, harvested and stored to extract FeMo-co. In some embodiments, the genes in the cells that encode for the synthesis of nitrogenase within that organism can be genetically modified to include a tag (e.g., string of histidine amino acids) fused to an end. Once expressed, the tag can facilitate the separation and purification of the component I protein of nitrogenase utilizing, e.g., liquid chromatography. In one example, adequate numbers of *Azotobacter vinelandii* bacterial cells are grown in a 150 liter fermenter and harvested in a 2 day procedure. Thereafter, in a 12 to 16 hour procedure, MoFe protein, component I of nitrogenase, is purified under oxygen free conditions. In an additional procedure, FeMo-co can then be extracted into N-methylformamide, an organic solvent, under strict anaerobic conditions.

Other host cells such as *Escherichia coli* can also be used for heterologous expression of FeMo-co. In some embodiments, using FeMo-co extracted from Component I protein from nitrogenase may be desirable since it is homologously expressed in *Azotobacter vinelandii*. Homologous expression in *A vinelandii* cells can, in some instances, provide larger amounts of FeMo-co in respect to the amount of hydrogenase yielded from the protein purification from heterologous expression.

CdSe.FeMo-co Complex

Figure 2:
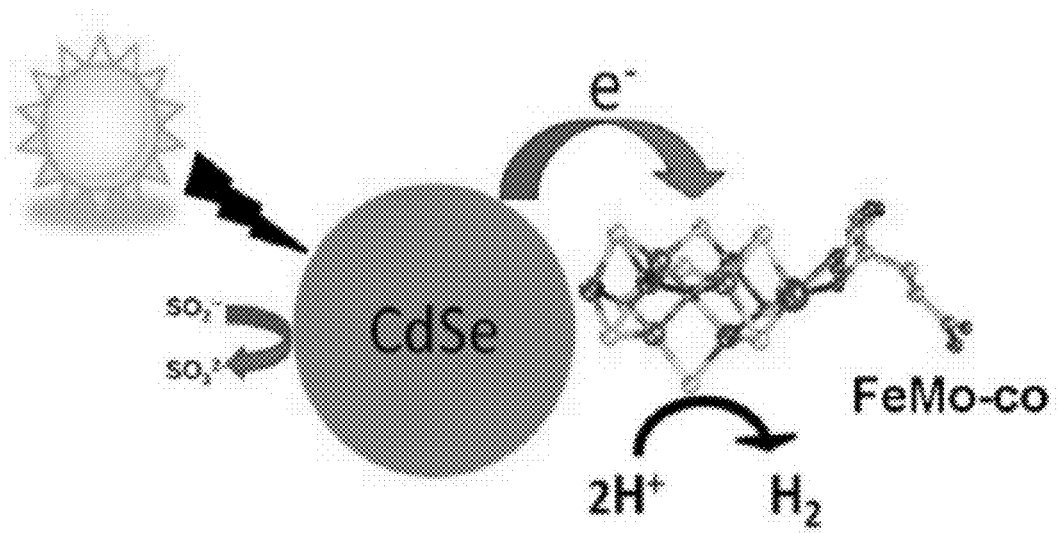
FIG. 2. Representation of CdSe Nanoparticles Complexed with FeMo-co. Visible light excites CdSe enabling photoreduction of FeMo-co that catalyzes the production of hydrogen from available protons in solution.

Toward the goal of developing a novel advanced material for photocatalytic $H_2$ production, a complex containing FeMo-co and CdSe, a photoreductive nanoparticle is provided by the present disclosure. Such a CdSe.FeMo-co system is a passive way to produce hydrogen as an alternative fuel source. The CdSe.FeMo-co system could photocatalytically generate $H_2$ is substantiated by the fact that CdSe nanoparticles are able to reduce methyl viologen ($MV^{2+}$) by photoactivation. The CdSe.$MV^{2+}$ system was illuminated and caused reduction of the $MV^{2+}$ where the reduced state was observed by transient absorption spectroscopy [14]. The reduction potentials of $MV^{2+}$ and FeMo-co are very close (−0.460 mV and −0.465 mV, respectively) [15, 16]. Therefore, CdSe can photo-reduce FeMo-co in the same way that it reduces $MV^{2+}$. With illumination of a CdSe.FeMo-co system, CdSe photo-reduces FeMo-co and then FeMo-co catalyzes the reduction of dissolved protons to evolve hydrogen (FIG. 2).

In certain embodiments, it is described herein how CdSe and FeMo-co are complexed, with and without a protein, in organic and aqueous media, and are used for generation of hydrogen. Because of the readily available source of solar energy, the generation of hydrogen through photo-catalysis represents a promising option to secure a sustainable energy source for the future.

In some embodiments, aqueous CdSe.FeMo-co may be advantageous over that in an organic solvent. For example, the presence of an organic solvent may limit the use or compatibility with most protein applications, or applications involving other biomolecules. Thus, in one embodiment, water soluble CdSe nanoparticles and FeMo-co are first prepared, and then mixed together under proper conditions to form a water soluble complex.

Water soluble CdSe nanoparticles are provided by the present disclosure. It should be noted that numerous attempts at synthesizing aqueous based CdSe particles have failed previously, since they were not found to be photoluminescent and therefore not photo-active. It was only through exhausting numerous synthetic strategies that the present disclosure identified a suitable method of making photo-active aqueous soluble CdSe nanoparticles. In some embodiments, synthesizing Water soluble CdSe nanoparticles includes first synthesizing CdSe nanoparticle surface capped with trioctylphosphine (TOP), and exchanging the surface capping agent with mercaptosuccinate to form the CdSe-MSA. In certain embodiments, the exchanging step is performed in methanol under reflux in the presence of a base such as tetrabutylammonium hydroxide.

In certain embodiments, to introduce FeMo-co into an aqueous system, a chaperone protein can be used. In one embodiment, NafY (nitrogen accessory factor Y), a FeMo-co insertase [60] is used to bind to FeMo-co. NafY protein is a 26 kDa chaperone protein that assists with insertion of completely assembled FeMo-co into the apo-MoFe protein. It has a high affinity for FeMo-co. From mutagenesis studies, His121 in NafY is suggested to bind FeMo-co, which is located on the surface of NafY [61]. NafY binds independently to FeMo-co or to the apo-MoFe protein (NifDK). The presence of NafY has been observed to stabilize apo-NifDK, and thereby prepares apo-NifDK for FeMo-co insertion [61]. After the insertion of FeMo-co into apo-NifDK, the NafY dissociates from the activated NifDK [62].

To assemble the CdSe.FeMo-co complexes of the present disclosure, an ordered procedure should be followed. In one example, the procedure includes: (a) providing a water soluble cadmium selenide nanoparticle (CdSe) surface capped with mercaptosuccinate (CdSe-MSA); (b) providing a NafY.FeMo-co complex comprising a NafY protein and an iron-molybdenum cofactor (FeMo-co); and (c) mixing the CdSe-MSA and the NafY.FeMo-co complex under anaerobic conditions to form a CdSe-MSA.NafY.FeMo-co system.

In some embodiments, photo-active CdSe nanoparticles that are in a particular size regimen (e.g., 2.4-2.7 nm) should be used. The sample concentration of both the CdSe nanoparticles and the FeMo-co can also be controlled (e.g., in a 1:1 molar ratio). Anaerobic conditions throughout the complex preparation are important. In addition, FeMo-co in N-methylformamide (NMF) solvent be added in a stepwise manner so as not to exceed 3% v/v NMF/NafY aqueous solvent during the process. This is to prevent the NMF from degrading the NafY protein. NafY has a high affinity for FeMo-co and during the additions of FeMo-co/NMF aliquots to the NafY solution, FeMo-co will quickly bind to the NafY. Once bound to NafY the FeMo-co is sequestered inside NafY. This is important so as not to expose the FeMo-co to aqueous solution and thereby hydrolyze the FeMo-co. The maintenance of strict anaerobic conditions facilitates this coupling. The next step is to add the NafY-.FeMo-co solution to the CdSe-MSA. When mixing CdSe-MSA and the NafY.FeMo-co, the addition of CdSe-MSA should not be performed before the dithionite concentration is increased so as to avoid quenching of the CdSe photoluminescence by the dithionite.

When combining CdSe NPs with FeMo-co, several considerations must be given. FeMo-co has a standard reduction potential of −465 mV. Methyl viologen's reduction potential has a similar value of −460 mV. It was reported that adsorbed methyl viologen was reduced by photoactivation of cadmium selenide, interrogated by transient absorption spectroscopy [63]. If FeMo-co could be introduced to cadmium selenide nano-particles and adsorb on the surface then once the cadmium selenide is illuminated and emitted electrons, then some novel chemistry could result. It was first necessary to establish that by adding the FeMo-co to a solution of CdSe, the FeMo-co would adsorb onto the surface of the CdSe. This can be demonstrated by showing that there is an interaction between the two.

Several steps were first carried out to prepare the reactants before the interaction could be demonstrated. First, CdSe nanoparticles were synthesized by high temperature pyrolysis. The CdSe quantum dots were capped with trioctylphosphine and solubilized in octadecene. Characterization showed that the dots were 2.4 nm in diameter and that they were very photoluminescent. Next, the CdSe needed to be aqueous soluble so a ligand exchange was carried out. This was done by a reflux in methanol reaction that facilitated the exchange of mercaptosuccinic acid for the trioctylphosphine on the surface of the CdSe nanoparticle. Characterization demonstrated that the CdSe nanoparticles were now 2.6 nm in diameter and that the photoluminescent property was slightly diminished; however, the nanoparticles did retain adequate photoluminescence to conduct further experiments.

Specifically, the photo-activity of the mercaptosuccinic capped CdSe nanoparticles was demonstrated by experiments with light driven reduction of adsorbed methyl viologen. Methyl viologen was added to CdSe and then over 30 second time intervals, UV-visible spectroscopy was measured with a time dependent absorbance increase at 605 nm (FIG. 8A) As more methyl viologen was reduced by the electron transfer from the light excited CdSe nanoparticle emission of electrons, there was a corresponding observable increase of blue colored solution. Performing ligand exchange on trioctylphosphine capped nanoparticles is known to diminish photo-activity of quantum dots; however, as the fluorescence characterization, FRET spectra and reduction of adsorbed methyl viologen demonstrations showed, the aqueous solubilized CdSe nanoparticles were adequately photo-active.

Figure 6A:
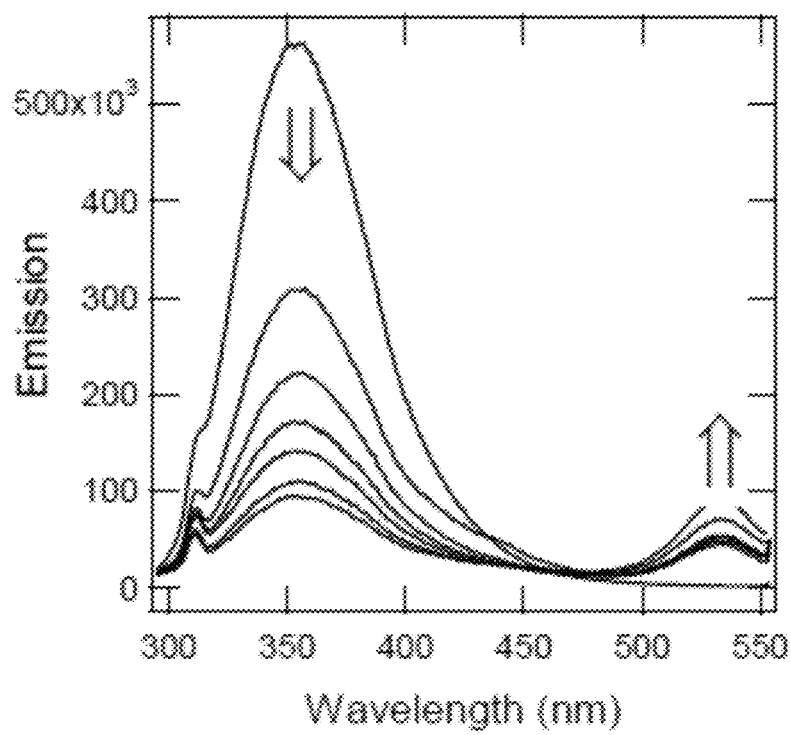
FIGS. 6A-6D. NafY Protein and CdSe-MSA Complex Formation Investigated by Fluorescence Quenching.
Figure 7:
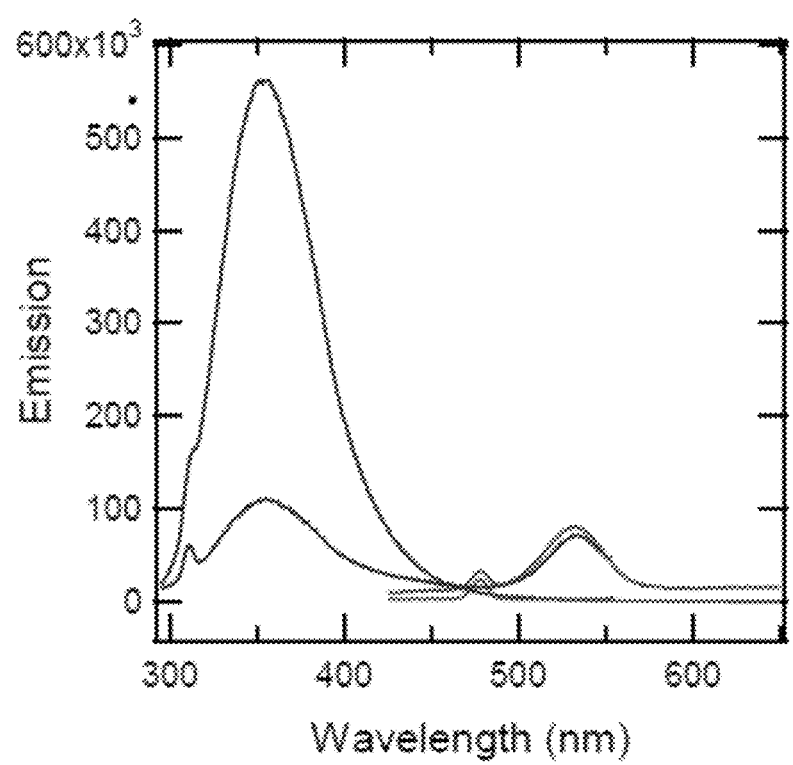
FIG. 7. FRET Emission in NafY-CdSe-MSA Complexed System Shown in Replots of Data from FIGS. 6A and 6B. Excitation of the NafY samples was at 280 nm. The emissions at 347 nm are NafY before (rust brown) and after (forest green) addition of 30 μL CdSe-MSA. The emission at 347 serves as the donor for the CdSe-MSA. The forest green peak shows a second emission that is the acceptor demonstrating FRET emission. The blue peak is the same sample with the addition of the CdSe-MSA excited at 410 nm and emitting at 532 nm. The pale green is NafY before the addition of CdSe-MSA excited at 410 nm.

Demonstrating that there was an interaction between CdSe and NafY protein utilized the tryptophan fluorescence inherent within polypeptide chains. Adding CdSe capped with mercaptosuccinic acid in aliquots demonstrated a concentration dependent quenching of the NafY protein fluorescence when exciting the sample at 280 nm (FIG. 6A). Interaction between CdSe and NafY was further demonstrated by Forster Resonance Energy Transfer (FRET) when exciting the NafY and CdSe samples at 280 nm and 410 nm (FIG. 7). The donor emission of NafY fluorescence emission excited the CdSe which served as the acceptor. The emission at 525 nm was that verified of CdSe confirmed by excitation of the sample at 410 nm and showing the same emission peak.

Figure 9:
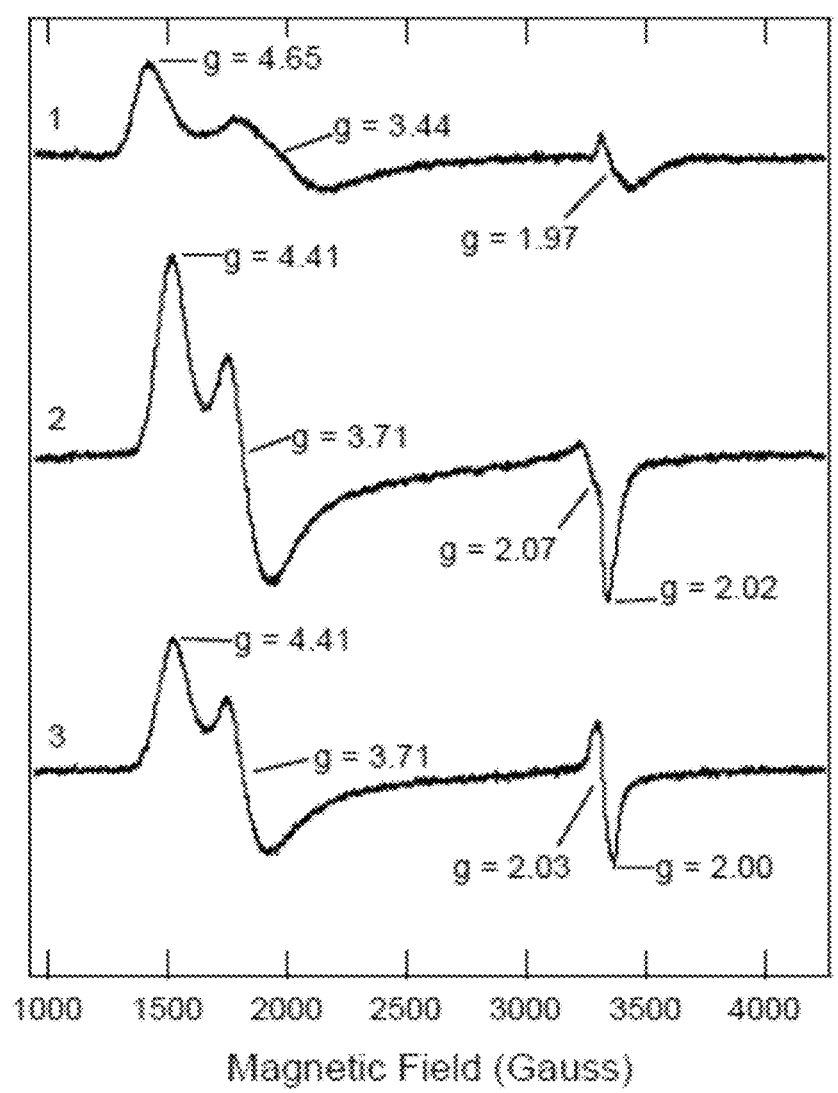
FIG. 9. CdSe-MSA and NafY.FeMo-co Complex Formation Investigated by EPR. EPR spectra are shown for 60 μM FeMo-co (trace 1); 200 μM NafY.FeMo-co (trace 2); and CdSe-MSA.NafY.FeMo-co (trace 3) with little change from the spectrum in Trace 2. CdSe-MSA (400 μM), NafY.FeMo-co (200 μM).
Figure 10:
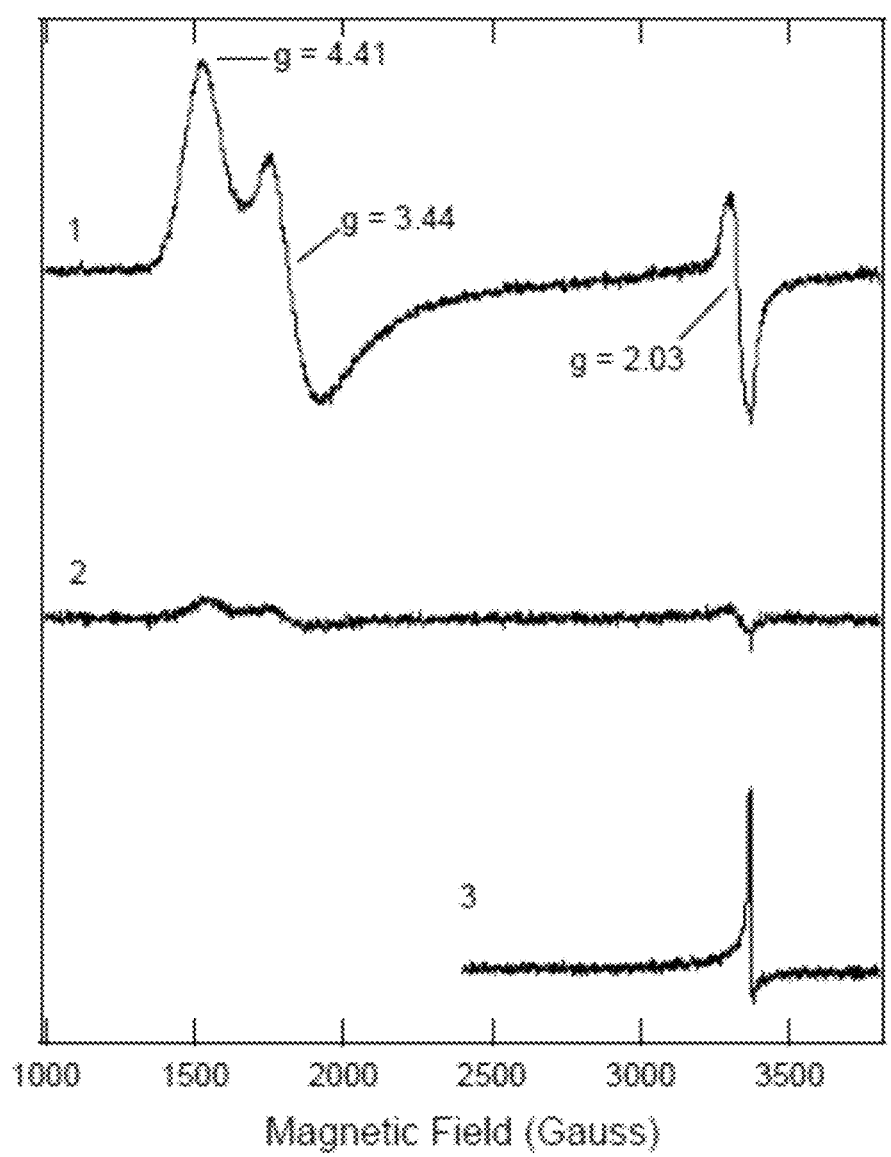
FIG. 10. Illumination of CdSe-MSA.NafY.FeMo-co Complex Characterized by EPR. EPR spectra are shown for CdSe-MSA.NafY.FeMo-co (trace 1), after illumination with a mercury lamp (trace 2) and after air exposure (trace 3).

Electron transfer between the CdSe and the adsorbed NafY.FeMo-co was interrogated by the use of electron paramagnetic resonance spectroscopy (EPR). Samples of CdSe.NafY.FeMo-co prepared in 2.0 mM sodium dithionite 25 mM Tris solution, pH 8.0, were made. The first set of EPR spectra showed that the NafY.FeMo-co system was intact after its addition and adsorption to the CdSe nanoparticles (FIG. 9). The CdSe.NafY.FeMo-co sample was thawed, subjected to ten seconds of intense illumination and then flash frozen. A second EPR was taken and showed an EPR silent state that was indicative of an electronic change. The light had driven an electron transfer to the FeMo-co indicated by a change in the oxidation state of the FeMo-co; the $S=3/2$ resting FeMo-co spin state had converted to a spin silent state. The electron could then be available for proton reduction (FIG. 10).

Figure 12A:
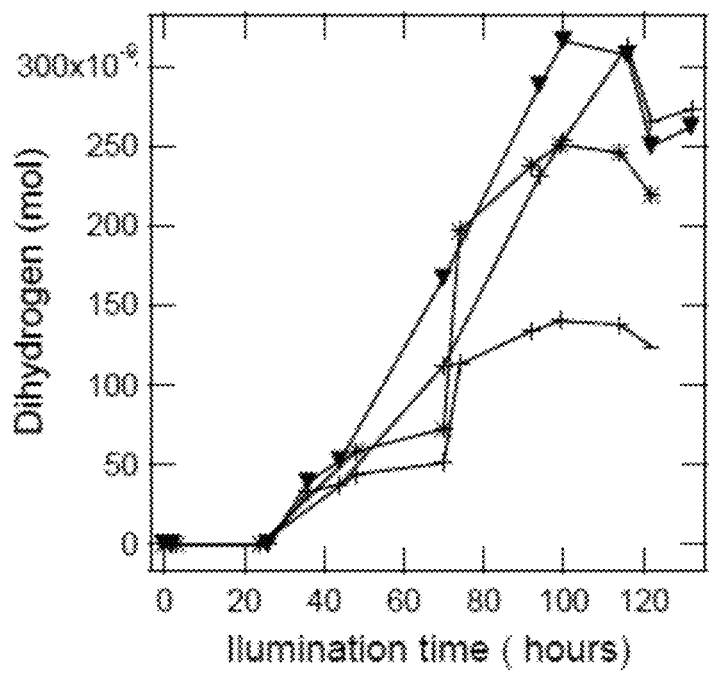
FIGS. 12A-12B. Time Dependent $H_2$ Production by a 1:1 CdSe-MSA.NaY.FeMo-co System.

In various embodiments, the CdSe.FeMo-co complexes of the present disclosure are capable of photocatalytically producing hydrogen when illuminated. Hydrogen generation experiments were initially set up with various CdSe to NafY.FeMo-co ratios in 25 mM Tris, pH 8.0, 2 mM sodium dithionite. In some embodiments, 1:1 CdSe:NafY.FeMo-co can be used. The purpose of the dithionite in excess was twofold. It served to preserve the anaerobicity of the sample and was a sacrificial electron donor to fill the electron hole generated by exciton creation by light energy. The samples were set up on a Peltier cooling device and exposed to a 500 watt hydrogen lamp. The temperature was at 28-30° C. The headgas was drawn and injected into gas chromatograph to detect hydrogen gas generation which continued until approximately 114 hours after sample set up. In four different experimental sets under the same reaction conditions, hydrogen was produced with a rate of 105.3 moles of $H_2$/mole of CdSe.NafY.FeMo-co (FIG. 12A). The rate could also be expressed as 0.069 μmol $H_2$/mg protein/hour. This is comparable to rates generated by other PSI/Pt/hydrogenase systems [68].

Some of the advantages of using CdSe versus some other photoactive materials include the band gap energy of CdSe and its ability to emit electrons when excited by light with the energy that is thermodynamically matched to the iron-molybdenum cofactor (FeMo-co) and its ability to reduce protons. The FeMo-co, in some embodiments, can be coordinated to its natural chaperone protein, NafY (26 kDa), which is less than half the size of the hydrogenases used in other hybrid systems. FeMo-co can be stabilized in NafY, which is an improvement over its extracted state, dissolved in N-methylformamide. Once charge separation is achieved versus the electron's tendency to relax back to the ground state, the close proximity to the surface of the CdSe facilitates more efficient electron transfer to the FeMo-co. Furthermore, the CdSe band gap energy is not too oxidative once the electron hole is generated as compared to $TiO_2$, another photoactive material used in some hybrid systems. $TiO_2$ tends to both oxidize amino acids within the polypeptide chain of the enzyme and also may oxidize water to form $O_2$ which would jeopardize the integrity of the NafY.FeMo-co. The CdSe.FeMo-co system also avoids the use of the expensive and rarely found platinum, used in many of the hybrid systems in literature where platinum is at risk to be poisoned by environmental contaminants and be rendered inactive.

Furthermore, it has been surprisingly found that a CdSe.NafY.FeMo-co system can produce hydrogen for a prolonged period of time (e.g., for at least 5 hours, at least 10 hours, at least 50 hours, or at least 90 hours, or longer) compared to the published systems which produce hydrogen for up to 4 hours at the most. In one example, the CdSe.NafY.FeMo-co system is operational for 114 hours, whereas other conventional systems were only operational for minutes or for a few hours.

Additional variables can be optimized to improve hydrogen production yield, rate and/or longevity. pH is probably the first. pH was initially at 8.0, the pH of the Tris buffer solution. The pH of the buffer can be reasonably lowered and thus provide more $H^+$ for reduction. In addition, the system can withstand warmer temperatures and this can help in shifting the equilibrium towards the formation of the $SO_2^-$, the radical monomer form of $S_2O_4^{2-}$, the real reactive species in the dithionite. It was found that in a temperature range of 2-40° C., the monomer form is favored at higher temperatures. Furthermore, dithionite concentration can be increased. Finally, a slight overpotential can be provided if the system is incorporated to a fuel cell. It is possible to explore depositing the CdSe.NafY.FeMo-co on a graphite electrode so that diffusion rates are not a limiting factor. Thus, the system demonstrated a stability and longevity that can be extended to make it adaptive for commercial applications.

In conclusion, there are many advantages to a CdSe.NafY.FeMo-co system compared to other hydrogen generation systems in the literature, such as:

- CdSe nanoparticles are relatively inexpensive to make and are reliably photo-active. They are stable for long periods. This is in contrast to the expensive catalyst, platinum, which is of limited availability, and is used in numerous other hybrid systems in research. Platinum is easily poisoned by environmental contaminants.
- CdSe, if provided with an adequate sacrificial electron donor is stable for long periods of time and withstands photo-degradation characteristic of other semiconductor systems such as CdS.
- The energy required to produce hydrogen is a good thermodynamic match for the electrons emitted from CdSe.
- FeMo-co is one of the most powerful catalysts in nature. It catalyzes the production of ammonia and hydrogen in ambient temperatures and pressures. In contrast, man-made catalysis to produce ammonia requires 450° C. and 200 atmospheres of pressure. In the absence of nitrogen, FeMo-co will catalyze the production of hydrogen gas as in this water based system in ambient temperatures and pressure.
- In the CdSe.NafY.FeMo-co system of the present disclosure, FeMo-co is bound to NafY (26 kDa), less than one half the size protein compared to hydrogenase (56 kDa) used in similar systems. NafY protein is the chaperone protein which is active to insert FeMo-co into the nitrogenase component protein after synthesis occurs. NafY.FeMo-co is stable, yet accessible for electron transfer from the photo-active CdSe. Efficient electron transfer reactions are all about the proximity of reactive components.
- Similar systems, one using hydrogenase and another with a component protein of nitrogenase, produced hydrogen for five minutes and 50 minutes, respectively. There are other systems using photosystem I as a light harvesting component combined with either platinum or hydrogenase which lasted for longer periods, but use the expensive platinum material. The CdSe.NafY.FeMo-co system of the present disclosure produced hydrogen for, e.g., 100 plus hours and has the potential to be optimized to perform for longer periods.
- The hydrogen produced by CdSe.NafY.FeMo-co system is pure versus hydrogen produced by steam reforming. Impurities in hydrogen streams are undesirable since they can poison expensive metal catalysts such as platinum in fuel cells.
- A practical application of the CdSe.NafY.FeMo-co system is to incorporate it with a fuel cell. As a result, fuel cells can be provided with a continuous flow of hydrogen from the CdSe.NafY.FeMo-co system to react it with oxygen from the air to enable production of electric current.

EXAMPLES

Aspects of the present teachings may be further understood in light of the following examples, which should not be construed as limiting the scope of the present teachings in any way.

1. Introduction

In the following examples, CdSe and FeMo-co were complexed with and without a protein, in organic and aqueous media, and were used for generation of hydrogen. First, to prove that a complex would form, fluorescence quenching was used to interrogate complex formation between chloroform soluble CdSe nanoparticles and FeMo-co, as well as between aqueous soluble CdSe and NafY protein and FeMo-co. Next, to show that electron transfer would occur, electron paramagnetic resonance spectroscopy was used. The complex with the most promise for hydrogen generation was the CdSe-MSA.NafY.FeMo-co system, which when illuminated with visible light evolved hydrogen consistently and for prolonged periods of time compared to published systems. The CdSe.FeMo-co system may prove to be a promising alternative fuel source.

2. Materials and Methods 2.1 UV-Vis Absorbance and Fluorescence Emission Spectroscopy UV-visible absorbance spectra were acquired on a Perkin-Elmer Lambda 750S spectrophotometer. Fluorescence emission was measured using a Horiba Jobin Yvon Fluoromax 4 Spectrofluorometer at excitation slit widths of 2 or 3 nm and emission slit widths of 2 or 3 nm.

2.2 Synthesis of CdSe-TOP Nanoparticles

CdSe-TOP quantum dots with particle sizes of 2.4 to 2.7 nm were synthesized using a high temperature pyrolysis method [14]. The CdSe nanoparticles with the capping agent, trioctylphosphine (TOP), were solubilized in chloroform and prepared according to published methods [17, 18]. The nanoparticles were stored anaerobically in the dark at 4° C. The quantum dots were characterized by UV-vis absorbance and fluorescence emission spectroscopy. The CdSe nanoparticle size was determined by noting the first absorption peak, using the published method relating absorbance to nanoparticle diameter. The calculated extinction coefficient based on the particle diameter was 59,598 $M^{-1}cm^{-1}$ that enabled the determination of CdSe nanoparticle concentration [19]. Absorbance ($\lambda_{max}$), was 515 nm and fluorescence emission ($Em_{max}$), when excited at 410 nm was 531 nm [20]. CdSe-TOP will be used to designate TOP capped CdSe that is soluble in organic solvents.

2.3 Purifications of MoFe Protein, NafY, and Extraction of FeMo-co

MoFe protein was purified from *Azotobacter vinelandii* strain DJ995, expressed with a polyhistidine tag fused on the C terminus of nifD, as previously described [21]. The host cell can also be engineered to express NifD fused to other tags known in the art to facilitate purification of the fusion protein. NifD is the α-subunit of MoFe protein (NifDK). MoFe protein purity was judged to be 95% pure using SDS-PAGE [22], stained with Coomassie blue. Quantification was performed by Biuret assay [23]. FeMo-co was acid extracted into N-methylformamide (NMF) solution using previously published methods [24], and quantified by assaying Fe concentration as previously described [25]. The degassed NMF solution was adjusted to a pH of 8.0 with triethylamine and sodium dithionite was anaerobically added to a final concentration of 1 mM. To assess FeMo-co activity, FeMo-co was added to an apo-form of the MoFe protein to form the holo-MoFe protein and assayed by measuring hydrogen evolution activity [26].

NafY was cloned from *Azotobacter vinelandii* (wild type) and expressed in *Escherichia coli* and purified according to previously published procedures [27]. Protein purity was assessed by SDS-PAGE and quantification was performed by the bicinchoninic acid assay method using bovine serum albumin as a standard [28].

2.4 Assembly of Complexes between CdSe-TOP and FeMo-co

All sample preparations were performed in anaerobic septum sealed cuvettes or vials, using standard Schlenk line techniques or performed in an anaerobic chamber with 5% (v/v) hydrogen/nitrogen and less than 1 ppm $O_2$. Gas tight syringes were used to perform liquid transfers for all experiments.

2.5 X-Band EPR Spectroscopy

X-band EPR spectra were recorded on a Bruker Elexsys E580 X-band spectrometer equipped with a Bruker standard rectangular TE102 resonator and fitted with an Oxford Instruments ESR900 helium flow cryostat. Modulation frequency was set at 100 kHz and modulation amplitude was set at 1.00 mT (10.0 G). The microwave frequency was approximately 9.45 GHz with the exact frequency noted for each spectrum and used for calculation of g values. All spectra were recorded at 5 K using a microwave power of 2.0 mW. Each trace was a sum of five scans unless stated otherwise.

2.6 Assembly of CdSe-MSA.NafY-FeMo-co Complexes

Water soluble CdSe nanoparticles were synthesized following a published procedure with some modifications. CdSe-TOP nanoparticles were synthesized by high temperature pyrolysis and dissolved in octadecene [30]. Characterization was performed by UV-vis absorbance ($\lambda_{max}$ ~515 nm), and fluorescence emission ($Em_{max}$ ~532 nm when excited at 410 nm). Size determination of the quantum dots was 2.4 nm diameter and the calculated extinction coefficient was 59,598 $M^{-1}$ $cm^{-1}$ [20]. To exchange the surface capping agent from trioctylphosphine to the aqueously soluble mercaptosuccinate, a reaction in methanol was performed under reflux at pH of 10. Fourfold molar excess of the quaternary base, tetrabutylammonium hydroxide, as compared to the added moles of mercaptosuccinate was used to fully deprotonate the mercaptosuccinic acid. The use of a solution of the base dissolved in methanol (40% w/v) was essential to avoid introducing any unnecessary water into the system.

During the work-up steps, the water soluble quantum dots were precipitated on the inner surface of the round bottom flask using a rotary evaporator, instead of precipitation by centrifugation as described in the published procedure. The quantum dots inside the flask were dried under vacuum overnight and resolubilized in aqueous 25 mM Tris, pH 8.0, the following day. The mercaptosuccinate functionalized CdSe quantum dots dissolved in 25 Mm Tris solution had an extinction coefficient of 73,681 $M^{-1}$ $cm^{-1}$[20]. Their diameter was calculated to be 2.6 nm with $\lambda_{max}$ at 525 nm and an Em. at 538 nm. CdSe-MSA will be used to designate the mercaptosuccinate capped water soluble quantum dots.

All samples with CdSe-MSA were set up in septum sealed cuvettes or vials using standard Schlenk line techniques or in an anaerobic chamber with 5% (v/v) hydrogen/nitrogen with less than 1 ppm $O_2$. Gas tight syringes were used to perform liquid and gaseous transfers in all the experiments.

A reaction between CdSe-MSA and methyl viologen was performed with aqueous soluble CdSe-MSA (720 nM) combined with methyl viologen (1.47 mM) and dithiothreitol (14.7 mM), with adaptations to a published method [30]. The samples were illuminated for 30 second intervals followed by UV-vis absorbance for a total time of eight minutes.

Preparation of the NafY.FeMo-co complex was performed using a modification of previously described procedures [31]. NafY in 25 mM Tris and FeMo-co in NMF solution were combined with stepwise aliquots of the FeMo-co such that the NMF solution did not exceed 3% (v/v) NMF so as to avoid denaturing of the protein.

2.7 Photo-catalyzed Hydrogen Production

CdSe-MSA and NafY.FeMo-co were mixed together in 3.0 mL anaerobic crimped seal vials in a total reaction volume of 1.5 mL, 25 mM Tris at pH 8.0, 0.2 mM $Na_2S_2O_4$, 2 μM to 16 μM CdSe-MSA nanoparticles and 2 μM NafY.FeMo-co.

The dithionite concentration was initially kept at 0.2 mM so as to allow the CdSe-MSA and NafY.FeMo-co to bind to each other with minimal interference from the dithionite. After one minute of mixing, the $Na_2S_2O_4$ concentration was increased to 2.0 mM. Prior to illumination, samples were thoroughly degassed and exchanged into argon by multiple rounds of vacuum and 3 psi of $O_2$ free argon. Reaction samples for the reduction of methyl viologen or hydrogen production experiments were illuminated using a 500 Watt halogen lamp. Samples were kept 8 cm from the light source. The samples were continuously illuminated and the temperature was kept at 30±2° C. Illumination times are indicated in relevant figure legends.

Assay for the evolution of hydrogen was performed by sampling (250 μL) the headgas of reaction vials using a gas-tight syringe and analyzing on a Hewlett Packard Series II 5890 Gas Chromatograph equipped with a Restek 13× 60/80 molecular sieve column and a thermal conductivity detector. Argon flow was set at 5.0 mL/min. Hydrogen peaks were standardized using quantitative hydrogen standards prepared in crimped seal vials of the same size and same headgas volume as the samples with 1.5 mL water volume according to published procedures [32].

3. Results

3.1 Assembly of CdSe-TOP.FeMo-co Complex

The intent for forming a CdSe-TOP.FeMo-co complex was to take advantage of the CdSe-TOP's photocatalytic activity and FeMo-co's ability to catalyze $H^+$ reduction. For the two components to work together and utilize solar energy to facilitate electron transfer for hydrogen production, the formation of a stable complex between CdSe-TOP and FeMo-co would be required.

CdSe-TOP nanoparticles are characteristically photoluminescent. Hence fluorescence emission may be used to interrogate interactions between CdSe-TOP and other chemical species [33]. Complex formation with another species may result in static quenching of the CdSe-TOP fluorescence emission. Static quenching may be observed if the interaction between different components allows for overlap of molecular orbitals [34]. Quenching of the CdSe-TOP fluorescence emission was used to determine if the added FeMo-co was bound to the surface of the nanoparticle.

The CdSe-TOP.FeMo-co system has some advantages as compared to CdSe in aqueous solvents. CdSe-TOP nanoparticles in organic solvents have significantly greater photo-activity as compared to the same sized CdSe nanoparticles in aqueous media (40 times more photoluminescence). CdSe-TOP nanoparticles exhibit the photo-activity due to their intrinsic quantum confinement characteristic. The quantization effects are observed because their excitons, excited electrons and their electron holes are confined within small regions of space. Although quantum dots are comprised of approximately 100 binary units of CdSe in three dimensional space, they are still small enough to exhibit the quantum properties of a single CdSe unit [35]. Quantum confinement also contributes to the observed property of nanoparticle color, i.e. the energy for excitation corresponding to the bandgap, which can be tuned by adjusting nanoparticle size within the parameters of its Bohr exciton radius (5.6 nm for CdSe) [36]. The size of the CdSe-TOP nanoparticles was dictated and controlled by managing reaction conditions such as temperature and time during its synthesis.

Another advantage to the CdSe-TOP.FeMo-co system was the ability to use chloroform as a solvent and its miscibility with NMF solution, which is used to extract FeMo-co from the MoFe protein. In addition, the NMF solution contains 1 mM sodium dithionite. The sodium dithionite serves two purposes in the CdSe-TOP.FeMo-co system of being an oxygen scavenger and as a source of electrons [26]. FeMo-co is very oxygen sensitive having an approximate half-life of about 30 seconds after air exposure [26], and the sodium dithionite prevents oxidative degradation of FeMo-co. When light excites CdSe-TOP, an electron is excited to a higher energy state moving into the conduction band. This generates an electron hole in CdSe's valence band. The dithionite acts as a sacrificial donor to quench the electron hole [37].

Figure 3A:
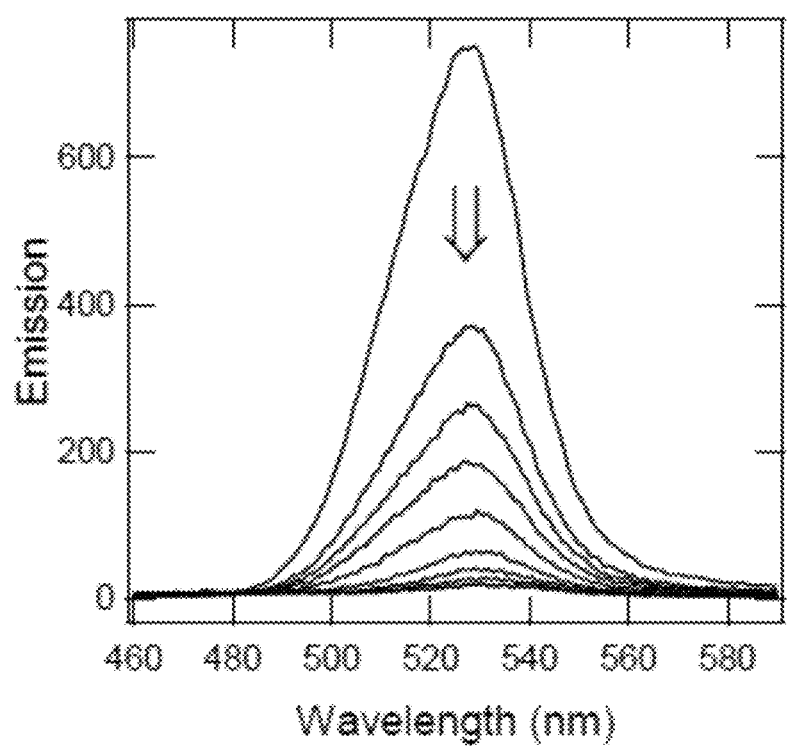
FIGS. 3A-3C. CdSe-TOP Fluorescence Quenching with Added FeMo-co or NMF.

As described earlier, fluorescence emission was used to probe the interaction between CdSe-TOP and FeMo-co. Incremental 1 μL additions of FeMo-co (60 μM stock) were made to a 10 μM solution of CdSe-TOP nanoparticles and the sample was inspected by both UV-vis absorbance and fluorescence emission spectroscopies after each addition. With the addition of either the FeMo-co or solvent NMF solution, the UV-vis absorbance (data not shown) did not change significantly, indicating that the integrity of the CdSe nanoparticles in solution was intact. In contrast, significant changes were observed in the fluorescence emission of CdSe-TOP. Progressive addition of FeMo-co to the CdSe-TOP solution resulted in the quenching of the CdSe-TOP fluorescence emission (FIGS. 3A and 3C).

Figure 3B:
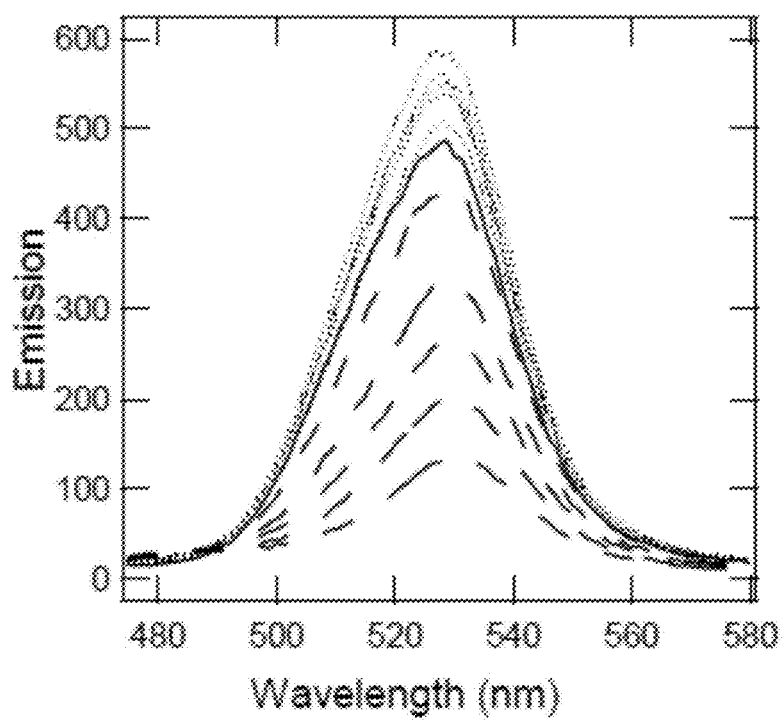
Figure 3C:
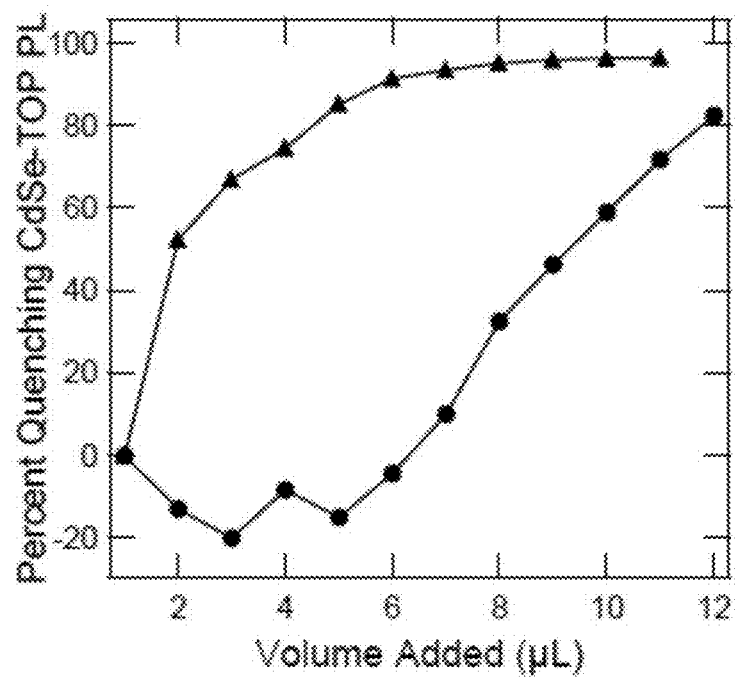

A similar titration was performed using the solvent NMF solution used for the extraction of FeMo-co to serve as a control (FIGS. 3B and 3C). The addition of NMF to the CdSe-TOP solution enhances its fluorescence intensity with the addition of the first 5 μL. This effect to enhance the fluorescence has been reported before [38]. The fluorescence intensity does decrease with the further addition, 6 to 10 μL, of the solvent NMF solution (FIG. 3B).

The degree of emission quenching with respect to the volume of either FeMo-co or NMF solution added (FIG. 3C), clearly shows a difference between the additions of FeMo-co solution and the additions of NMF solution. The addition of only 5 μL of FeMo-co (60 μM in solution) was sufficient to quench 90% of the CdSe-TOP fluorescence emission. In comparison, only 10% of the fluorescence emission was quenched with the addition of an equivalent volume of the solvent NMF solution. Furthermore, quenching of the CdSe-TOP fluorescence by FeMo-co seems to saturate, somewhat suggesting a specific interaction. These data indicate that the CdSe-TOP nanoparticles and the FeMo-co do form a complex. Additionally, the CdSe-TOP quantum dots that were most efficient for forming a complex were in the size range of 2.4 to 2.7 nm diameter.

Despite the demonstrated fluorescence quenching of CdSe-TOP by the addition of FeMo-co, which suggests the formation of a complex, a question persisted whether the quenching is due to binding of FeMo-co that is structurally intact. To test this, air-oxidized FeMo-co was added to CdSe-TOP. If the FeMo-co had degraded during the formation of the complex, quenching of the CdSe-TOP fluorescence would not be likely.

Figure 4:
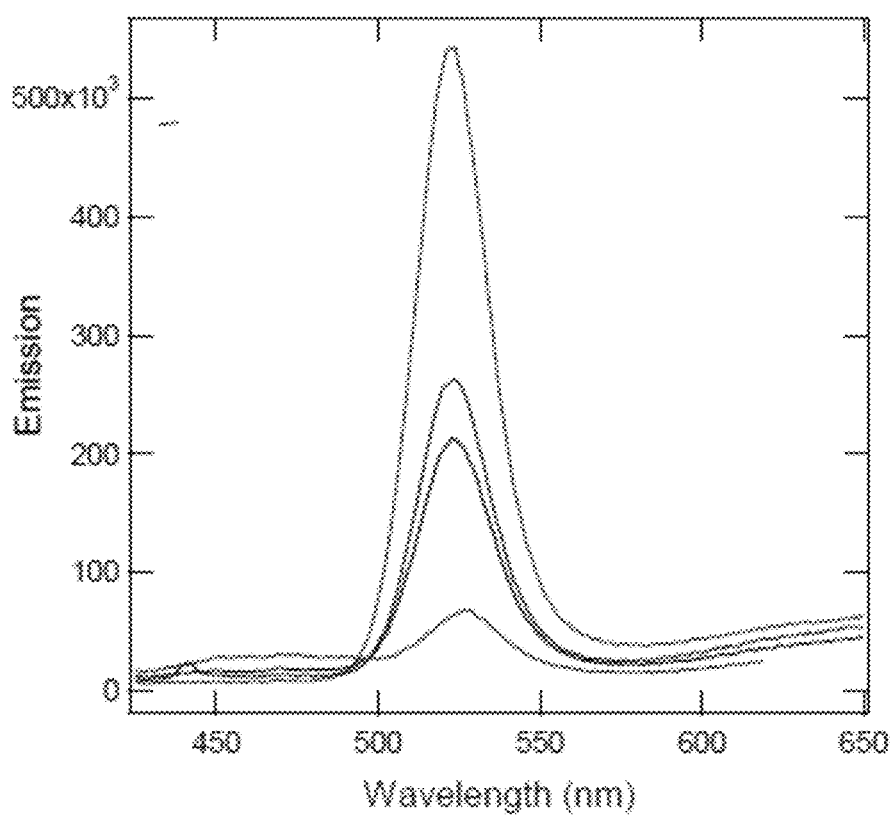
FIG. 4. CdSe-TOP Fluorescence Quenching by FeMo-co. The red trace is the control fluorescence emission spectrum of CdSe-TOP without any quencher. The blue trace is fluorescence emission spectrum of CdSe-TOP quenched by addition of the solvent NMF solution. The black line is the fluorescence emission spectrum with addition of air oxidized FeMo-co to CdSe-TOP. The green line is the emission spectrum of FeMo-co added to CdSe-TOP.

Three samples of CdSe-TOP (10 μM) were inspected by UV-vis absorbance and fluorescence emission before and after six μL additions of 1) 60 μM FeMo-co, 2) air exposed degraded FeMo-co of the same concentration, or 3) solvent NMF solution. Addition of FeMo-co quenched 88% of fluorescence from CdSe-TOP (FIG. 4 and Table 1), and addition of the solvent NMF solution caused 52% quenching, which represents a similar degree of fluorescence quenching in the titration experiments above. Significantly, the addition of degraded FeMo-co sample showed 61% of quenching, which is comparable to the extent of quenching observed with addition of the solvent NMF solution. Since the air exposed degraded FeMo-co was in NMF solution, the limited fluorescence quenching observed with the degraded $Fe^{2+/3+}$ was close to the fluorescence quenching observed with the addition of the same amount of NMF solution. Thus, structurally intact FeMo-co is binding to CdSe-TOP nanoparticles, causing CdSe-TOP fluorescence quenching. The fluorescence quenching observed is not due to potential dissolved $Fe^{2+/3+}$ in solution from degraded FeMo-co.

TABLE 1

Percent Quenching of CdSe-TOP Fluorescence by FeMo-co

| Additions to CdSe-TOP | Percent Quenching* |
| --- | --- |
| NMF, 0.1 mM dithionite | 51.7 |
| Oxidized FeMo-co | 60.7 |
| Active FeMo-co (0.36 μM) | 87.7 |

*CdSe-TOP fluorescence emission without additions is 518,000 arbitrary units. Percent quenching is a measurement of CdSe-TOP fluorescence after addition of reagents subtracted from fluorescence without the additions divided by fluorescence without additions times 100.

3.2 EPR Characterization of CdSe-TOP-FeMo-co Complex

EPR spectroscopic analysis of Fe—S clusters allows for investigation of electronic structures, electronic spin states and configurations. Changes observed in characteristic signals can possibly indicate a different electronic spin state or configuration. Oxidation state changes can also be observed after electron transfers [39]. FeMo-co has a characteristic $S=3/2$ spin state signal in its dithionite reduced resting state and also an analogous signal in the dithionite reduced holo-enzyme [40]. The CdSe-TOP nanoparticles show no EPR signal.

The fluorescence emission characterization of CdSe-TOP with added FeMo-co had suggested that CdSe-TOP.FeMo-co had formed a complex due to the quenching of fluorescence emission of the CdSe-TOP. With illumination of the CdSe-TOP, excited electrons could be transferred to the FeMo-co adsorbed on the CdSe-TOP surface with a potential observation of a change in the FeMo-co EPR signal due to an alteration in its electronic structure.

To achieve concentrations appropriate for EPR experiments (>100 μM of EPR active species), a much higher concentration of the CdSe-TOP nanoparticles were required. To achieve such a concentration, CdSe-TOP was precipitated and then resuspended in a minimal volume of an alternative solvent. Tests for solubility of the precipitated CdSe-TOP nanoparticles were performed in three different solvents. In microcentrifuge tubes, 300 μL of 100 μM CdSe-TOP nanoparticles were precipitated with the addition of 1.0 mL of ethanol and then pelleted by centrifugation (5030×g, for five minutes). The CdSe-TOP pellet was then resolubilized in 300 μL of three different solvents: NMF, acetone and ethyl acetate. The CdSe-TOP nanoparticles were soluble in the NMF and the ethyl acetate, but were insoluble in the acetone. NMF was chosen to be the solvent for the EPR experiments since NMF is the best known solvent for stabilizing FeMo-co and it was observed to be miscible with chloroform.

To inspect if the CdSe-TOP.FeMo-co complex would stay intact during the ethanol precipitation and resolubilization to enable concentration of the sample, CdSe-TOP before and after mixing with FeMo-co were characterized by UV-vis absorbance and fluorescence emission. Concentrations of reagents were the same as used in the fluorescence emission experiments. Ethanol was added to the CdSe-TOP.FeMo-co sample and was centrifuged at 5030×g for five minutes. The pellet was resolubilized in chloroform and the fluorescence emission spectrum showed no change from before the ethanol precipitation. The UV-vis spectra also showed no changes, and thus the CdSe-TOP.FeMo-co complex appeared to be intact after one ethanol wash.

Samples for EPR spectroscopy were prepared by mixing 3.0 mL CdSe-TOP (400 μM) with 0.67 mL FeMo-co (60 μM) and then precipitating with the addition of 10.0 mL of ethanol with rapid mixing on a vortexer. The sample was centrifuged (5030×g, for five minutes) to pellet the precipitated CdSe-TOP.FeMo-co. The pellet was solubilized by adding 250 μL of solvent NMF solution and vortexed. The sample was injected into a sealed anaerobic 4 mm quartz EPR tube and frozen in liquid nitrogen.

Figure 5:
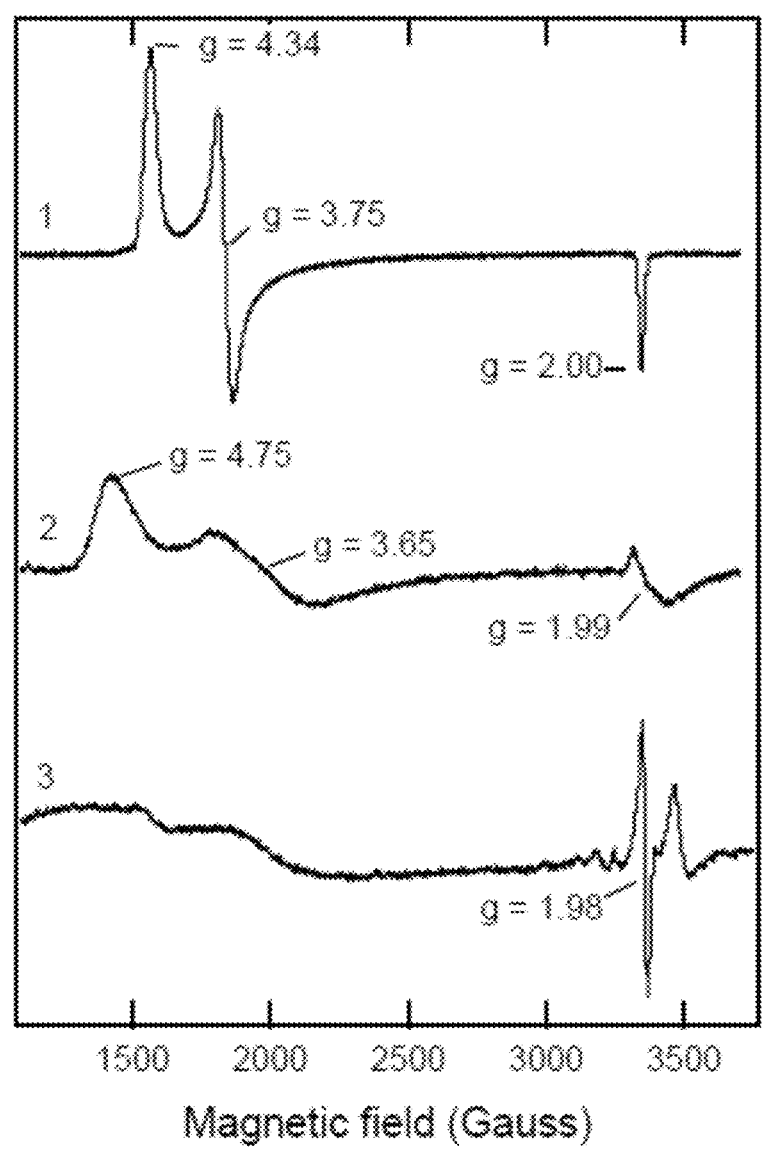
FIG. 5. CdSe-TOP.FeMo-co System Investigated by EPR. EPR spectra are shown for MoFe protein (180 μM) (trace 1), FeMo-co (60 μM) (trace 2) and CdSe-TOP.FeMo-co complex with CdSe-TOP (2.5 mM), FeMo-co (200 μM) (trace 3). Inflection points for the EPR absorption peaks are indicated by g-values.

The three control samples were as follows. The first control, CdSe-TOP, showed no EPR signal (not shown). The second control was that of 180 μM MoFe protein (2 FeMo-co clusters per protein molecule), (FIG. 5, Trace 1). The third control was that of 60 μM FeMo-co (FIG. 5, Trace 2) [41, 42].

The EPR inspection of the CdSe-TOP.FeMo-co (FIG. 5, Trace 3) shows significant changes compared to the MoFe protein or isolated FeMo-co. First, the EPR signal at g=4.3, 3.7 and 2.0, representing the S=3/2 spin state, is largely diminished and the S=1/2 spin state sub manifold signal had a g value of 1.99. Second, a significant new signal at g=1.98 and 1.97 is observed. Significantly, an EPR signal in this region of the spectra is from an S=1/2 spin state and suggests a change in electronic spin state, possibly due to reduction of the S=3/2 state of FeMo-co. Similar S=1/2 spin state signals have been observed with several trapped turnover intermediates of MoFe proteins and MoFe protein variants [43]. Such intermediates are associated with turnover states that are relevant to the mechanisms of substrate reduction for various substrates. Another S=1/2 spin state signal has been observed in a trapped state during proton reduction by FeMo-co in a nitrogenase α-70$^{He}$ MoFe protein variant [44]. Thus, the S=1/2 spin state in this experiment may be interpreted to indicate an electronic change in FeMo-co.

To further probe if the change in electronic spin state observed for the CdSe-TOP.FeMo-co may indeed be due to light catalyzed electron transfer from the CdSe, light dependent experiments were performed. FeMo-co should appear in the resting state with its S=3/2 spin state signal if there would be no photo-initiated electron transfer from the CdSe-TOP. An additional sample was prepared as the CdSe-TOP.FeMo-co sample in the light; however, before being frozen in the EPR tube it was exposed to air. This sample would verify that the new S=1/2 EPR signal was indeed a reduced state of FeMo-co and not $Fe^{2+/3+}$ ions in solution from degraded FeMo-co. Preparation of these samples in the dark were met with technical difficulties and EPR inspection of these samples yielded no interpretable data.

3.3 Assembly of CdSe-Mercaptosuccinic Acid.NafY.FeMo-co Complex

CdSe-TOP quantum dots in organic solvents are well known for their photo-activity, but the presence of an organic solvent limits their use with most protein applications. Three approaches to achieve water soluble CdSe quantum dots have been reported [45]. One is by a direct synthesis method which uses an arrested precipitation technique in aqueous media [46]. A second synthetic method encapsulates the organically soluble quantum dot in a polymerized silica shell functionalized with polar groups or an amphiphilic polymer coating that can significantly add to the quantum dot diameter [47]. Third, a ligand exchange method replaces the capping agent on the nanoparticle from trioctylphosphine or trioctylphosphine oxide with a mercapto-carboxylic acid [48].

A disadvantage with water soluble nanoparticles is their tendency to be less photo-active than their organic counterparts. If there is a lack of coordinated surface atoms, then there will be trapped states on the surface of the quantum dot that lie within the band gap. When light illuminates the nanoparticle and excites electrons to the conduction band, there will be more alternative pathways available for relaxation back to the ground state via the trapped states [48]. Thus the desired energy or electron transfer to any adsorbed surface species may not occur. The challenge was to determine the best consistent method to achieve the most photo-active aqueous soluble quantum dots.

Methods to produce the most luminescent quantum dot were explored through two efforts to directly synthesize the quantum dots [49, 50], and by three methods to exchange the capping agent [29, 51, 52]. Capping agents affect the photoluminescent properties of the nanoparticles. The most luminescent quantum dots with a target diameter (2.4 to 2.6 nm) were produced by a published method with some modifications using previously unused mercaptosuccinic acid (MSA), as the capping agent [29]. The previous complex between CdSe-TOP and FeMo-co took advantage of both reactants being in organic solvents. When isolated FeMo-co is mixed in water, even though kept anaerobic, the FeMo-co quickly hydrolyzes. For FeMo-co to combine with aqueous CdSe and remain intact, complexation to proteins was required.

NafY is a low molecular weight protein that binds FeMo-co with high affinity ($K_d$ of 62 nM) [27]. Combining FeMo-co with NafY and conjugating this species to CdSe-MSA may be a useful way to place the FeMo-co in close proximity to the photo-reducing CdSe-MSA. The NafY.FeMo-co conjugated to CdSe in a Tris buffered system would be a means for isolated FeMo-co bound to NafY to be in an aqueous system. The 26 kDa NafY.FeMo-co system has a further advantage, compared to the 250 kDa MoFe protein that contains FeMo-co in a more buried configuration, of being smaller and of providing better accessibility to FeMo-co. Furthermore, the aqueous solvent would be a better proton source for hydrogen evolution.

Although aqueous CdSe quantum dots are less luminescent (by a factor of 40), than CdSe in an organic solvent of the same diameter, thus indicating a lower quantum yield, their ability to be involved in electron transfer was anticipated. Inspection of the CdSe-MSA nanoparticles was performed to determine their capability to form complexes and their photoactive capability to transfer electrons to FeMo-co and thereby perform interesting and useful chemistry.

To use CdSe-MSA in experiments with a FeMo-co species, demonstration of CdSe-MSA forming a complex with proteins was necessary. CdSe-MSA was added in incremental amounts to bovine serum albumin (BSA) according to a published method and thereby demonstrating complex formation between the two reagents [54]. The published procedure had used CdSe capped with mercaptoacetic acid instead of the mercaptosuccinic acid capping the CdSe in this study. The samples were excited at 280 and 410 nm in a fluorescence emission investigation. Control samples of BSA alone and CdSe-MSA alone were excited at both wavelengths with no observable changes seen in the samples.

Emission at 347 nm was from the BSA and emission from the 532 nm was attributed to the CdSe-MSA. The BSA fluorescence emission was quenched 78% with the addition of 300 µL of CdSe-MSA. The ratio of the two components, BSA:CdSe-MSA, was 1:3.5. The conclusion was that CdSe-MSA and BSA protein had formed a complex.

Figure 6B:
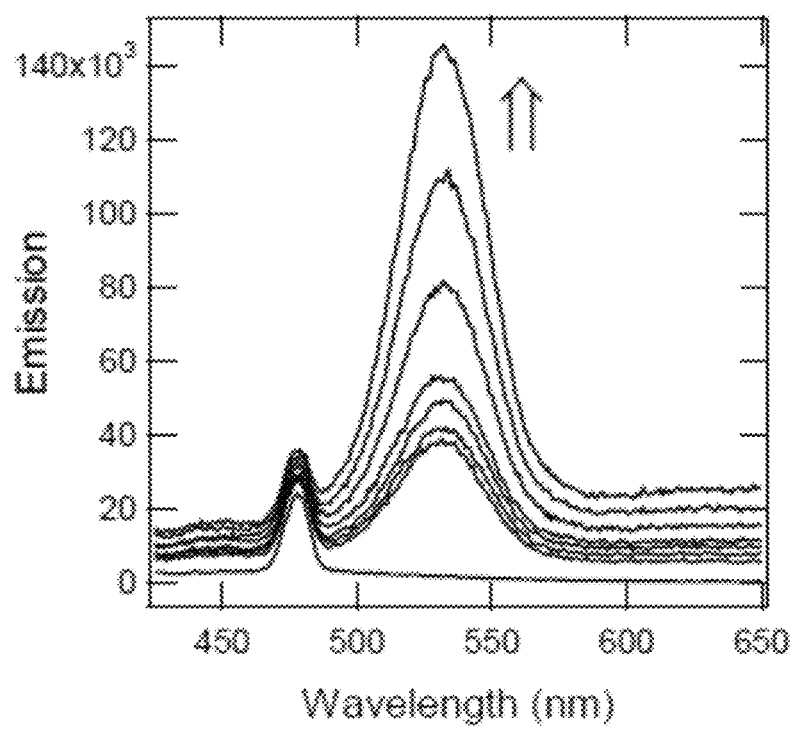
Figure 6C:
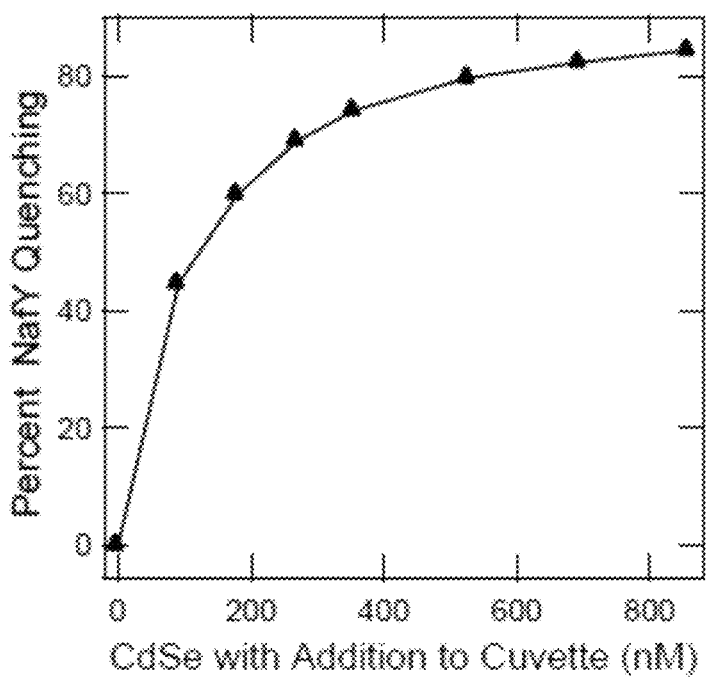
Figure 6D:
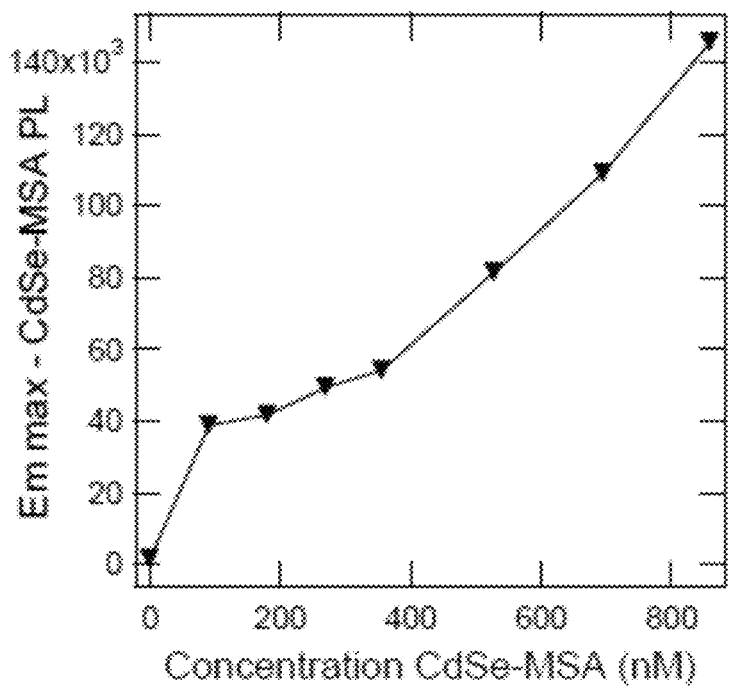

To probe complex formation between CdSe-MSA and NafY protein, the two were combined by adding incremental amounts of CdSe (14.6 µM stock) to NafY (500 nM) (FIGS. 6A and 6B). The sample was excited at 280 nm to observe tryptophan emission at 347 nm. The sample was also excited at 410 nm to verify that the observed peak at 532 nm could be attributed to the CdSe-MSA being added in increasing amounts. Eighty percent of the NafY fluorescence quenching was observed with 30 µL addition of CdSe-MSA, which is a 1:1 ratio between NafY.CdSe-MSA (FIG. 6B). A NafY control sample and a CdSe-MSA control sample showed no changes when excited at 280 nm and 410 nm. FIG. 6C shows the data from 6A replotted as percent quenching of NafY fluorescence versus concentration of CdSe-MSA. FIG. 6D shows the data from FIG. 6B replotted as CdSe-MSA fluorescence emission versus concentration of CdSe-MSA.

Additionally, Forster resonance energy transfer (FRET), could be interpreted from the fluorescence emission experiments. Two sets of emissions (347 nm and 532 nm) were observed (FIG. 7). Emission at 347 nm is from excitation of the tryptophans in NafY protein that acts as a donor for CdSe-MSA, which emits at 532 nm. The first emission at 347 nm (rust brown trace) shows NafY before addition of CdSe-MSA. The second emission (forest green trace) exhibits quenching of NafY fluorescence along with an acceptor emission at 532 nm from CdSe-MSA demonstrating FRET. When the sample was excited at 410 nm, the emission at 532 overlapped the emission observed with excitation at 280 nm confirming that the 532 nm emission was indeed from CdSe-MSA. FRET emission can only be observed when two species are close in proximity hence the conclusion was that NafY and CdSe-MSA had formed a complex.

To address the issue of lesser photo-activity of the water soluble quantum dots as compared to the organically solvated nanoparticles, an experiment with aqueous CdSe-MSA nanoparticles was performed. The hypothesis was that despite the photo-activity being less, the water soluble CdSe-MSA quantum dots would be able to perform a photo-induced electron transfer to a complexed species adsorbed onto their surface. To test the photocatalytic reduction activity, methyl viologen was combined with and CdSe-MSA. Dithiothreitol (DTT) would be used as a sacrificial electron donor to refill electron holes generated after electrons were excited to the conduction band from the valence band in CdSe-MSA. Reduction of the methyl viologen, $MV^{2+}$, was monitored by increasing absorbance peaks at 395 nm and at 603 nm with increasing times of illumination.

CdSe-MSA (720 nM), methyl viologen (1.47 mM) and dithiothreitol (14.7 mM), were combined and monitored by UV-vis absorbance. The sample was illuminated for 30 seconds and followed by UV-vis absorbance. This process was repeated for a total of eight minutes. To further test the photocatalytic ability of the system, the sample was first exposed to air to oxidize the reduced methyl viologen. Next, the cuvette was resealed and put on the manifold to make the headspace anaerobic by replacing it with argon. The photo-induced reduction experiment was repeated. Another air oxidation was followed by a third repetition of the experimental procedure. The first control sample was a solution of methyl viologen and dithiothreitol which underwent the same illumination times and UV-vis absorbance characterization. The second control was the CdSe-MSA for which the same experimental procedure was followed. A third sample was set up with the three reactants and kept in the dark for 16 hours.

Figure 8A:
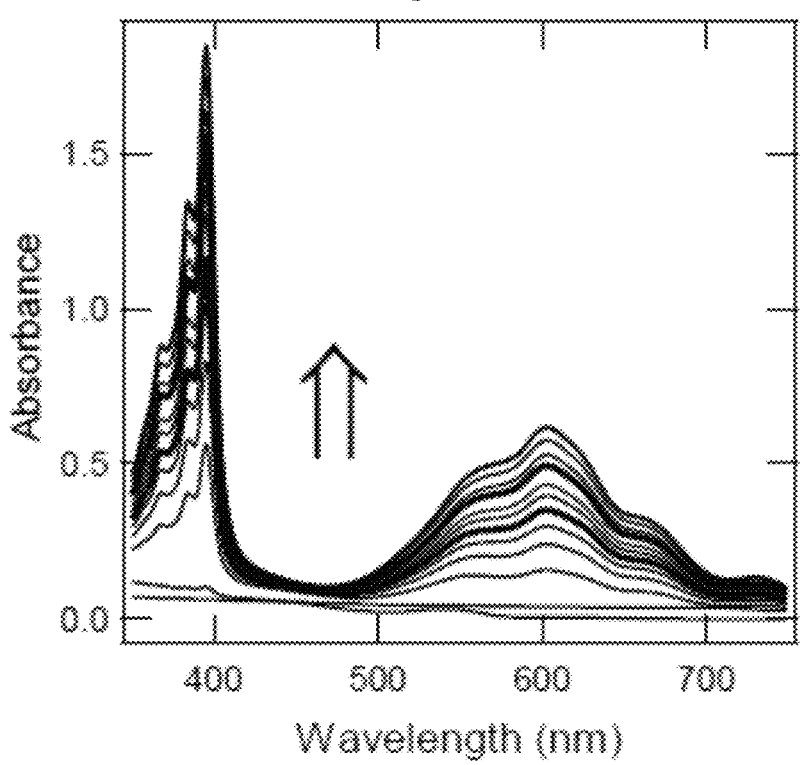
FIGS. 8A-8B. Photo-activated Time Dependent Reduction of $MV^{2+}$ by Excited CdSe-MSA.
Figure 8B:
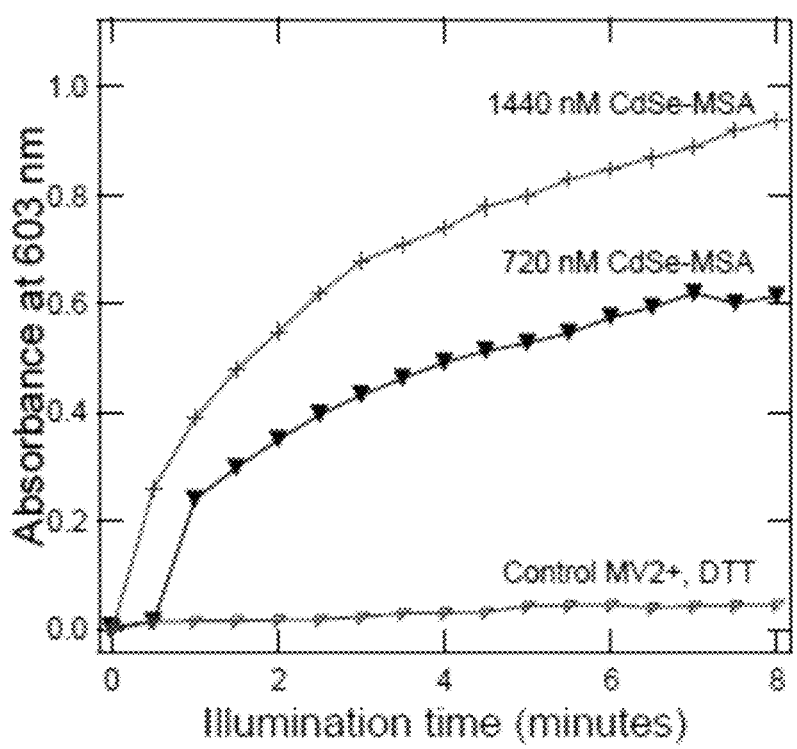

The results show increasing absorbance at both 395 nm and at 603 nm with increasing periods of illumination (FIG. 8A). The data for the absorbance at 603 nm was replotted as absorbance intensity versus time of illumination (FIG. 8B). After exposing the sample to air and repeating the illumination and UV-vis absorbance measurements, the sample again demonstrated increasing absorbance at 395 and 603 nm with increasing periods of illumination. Interestingly, the CdSe-MSA-methyl viologen solution turned progressively more intense in blue color with increasing periods of illumination, indicative of absorption at 603 nm. When the sample was exposed to air, it lost the blue color and was orange from the CdSe.

When the second round of illumination progressed the blue color returned to the sample. When the third repetition was performed, the same results were observed. The three controls showed no increasing absorbance at 395 nm or 603 nm with illumination. Additionally a concentration dependent experiment was performed with twice the CdSe-MSA (1.4 mM). The results showed that the absorbance peak at 603 nm increased more rapidly with the higher concentration of CdSe-MSA and thus showed a general trend of concentration dependence in the photo-reduction of methyl viologen (FIG. 8B). The conclusion was that the CdSe-MSA quantum dots were photoactive and able to perform photo-reduction of adsorbed species, $MV^{2+}$ in this case, when illuminated with intense visible light.

3.4 EPR Characterization of CdSe-MSA.NafY.FeMo-co

Experiments above present evidence that the CdSe-MSA will complex with the NafY protein and that CdSe-MSA is able to photo-reduce a species adsorbed onto its surface upon exposure to visible light. Thus, NafY.FeMo-co being close in proximity to CdSe-MSA should allow photo catalyzed reduction and possible post-illumination changes in the electronic structure of FeMo-co that could be observed by EPR spectroscopy.

NafY.FeMo-co samples were prepared prior to forming a complex with the CdSe-MSA. NafY protein was diluted to approximately 1.0 M in 25 mM Tris, pH 8.0, 0.5 mM sodium dithionite in a stirred ultrafiltration cell fitted with a YM10 membrane (Millipore). To prevent precipitation of NafY, additions of FeMo-co to the stirred cell ultrafiltration device containing NafY were made such that the NMF, solvating FeMo-co, did not exceed 3% (v/v). Repeated concentration and dilution steps were performed with each addition of FeMo-co. After the last addition of FeMo-co, 1.5 mL of degassed CdSe-MSA (30 µM) with 0.4 mM sodium dithionite was added. The solution was concentrated further to minimize the volume and then transferred to a 30,000 MWCO Centricon (Millipore) and kept anaerobic in JA-20 centrifuge tubes. Centrifugation was performed at a centrifugal force of 5000×g to reach the desired concentration. The sample was then injected into 4 mm EPR quartz tubes and frozen in liquid nitrogen. The final concentration of the sample was 400 µM CdSe-MSA, 200 µM NafY.FeMo-co.

Control samples were as follows. The first was a FeMo-co sample used to comprise the CdSe-MSA.NafY.FeMo-co samples. The second control was a NafY.FeMo-co sample. The third control was the CdSe-MSA.NafY.FeMo-co sample prepared as previously described under strict anaerobic conditions throughout, but before being frozen it was exposed to air. With air exposure, FeMo-co should oxidatively degrade, resulting in ferrous and/or ferric ions in solution. This control sample would demonstrate that any change seen with the FeMo-co signal, did not arise from dissolved iron in solution. One last control sample was that of CdSe-MSA alone at a concentration of 400 µM.

The FeMo-co control spectrum showed an EPR signal (g=4.65, 3.44 and 1.97) for an S=3/2 spin state, characteristic of its dithionite reduced state when extracted into solvent NMF solution (FIG. 9, Trace 1) [42]. Compared to the MoFe protein, with FeMo-co in the active site, the EPR spectrum for extracted FeMo-co was of a similar line shape, only broader. There were also comparable principal g-values, indicating that the general electronic structure was coincident. Binding of FeMo-co to NafY as in the NafY.FeMo-co yields a similar spectrum with g=4.41, 3.71 and 2.07 (FIG. 9, Trace 2), indicative of an S=3/2 spin state [27]. The binding of NafY does sharpen the line shape and is consistent with an additional ligand to FeMo-co, indicating covalent bonding between NafY and FeMo-co.

EPR characterization of the CdSe-MSA.NafY.FeMo-co sample (FIG. 9, Trace 3) showed an EPR signal for the S=3/2 spin state, very similar to that of NafY.FeMo-co, significantly indicating that the electronic structure of FeMo-co bound to NafY was not being perturbed when the protein was interacting with the CdSe. There was a change in the g=2 portion of the signal, corresponding to the S=1/2 submanifold, but the rest of the signal (g=4.41 and 3.71) remained unchanged. Hence, the structural integrity of FeMo-co, both molecular and electronic, should not be affected in this complex. This meant that FeMo-co survived the process and procedure for formation of the CdSe-MSA.FeMo-co ternary complex and would be suitable for photo-reduction.

The effect of light on the CdSe-MSA.NafY.FeMo-co sample was examined. The sample was sealed and thawed to room temperature anaerobically. The sample was exposed to a high intensity light for ten seconds. The sample was then immediately frozen in a hexanes-liquid nitrogen slush bath and re-characterized by EPR. The EPR spectrum (FIG. 10, Trace 2), showed significant change as compared to this same sample's previous EPR spectrum (FIG. 10, Trace 1, duplicate of FIG. 9, Trace 3). The post illuminated sample shows a largely diminished EPR intensity for a species with the same line shape as the S=3/2 state prior to illumination. The diminishment in signal intensity corresponds to a change in the population of S=3/2 spin state to some other EPR silent state, suggesting that illumination initiated an electron transfer from CdSe-MSA to the adsorbed NafY-.FeMo-co and therefore reducing it. This illuminated sample was then rethawed again, allowed to air oxidize, and refrozen. EPR inspection of the sample after air exposure (FIG. 10, Trace 3), shows a sharp signal at g=2.0, clearly from ferric irons. Thus, the conclusion was that upon exposure to intense light, the electronic state of FeMo-co changed due to a possible electron transfer from the CdSe-MSA to the NafY.FeMo-co.

3.5 Photocatalyzed Hydrogen Generation Experiments

Figure 11:
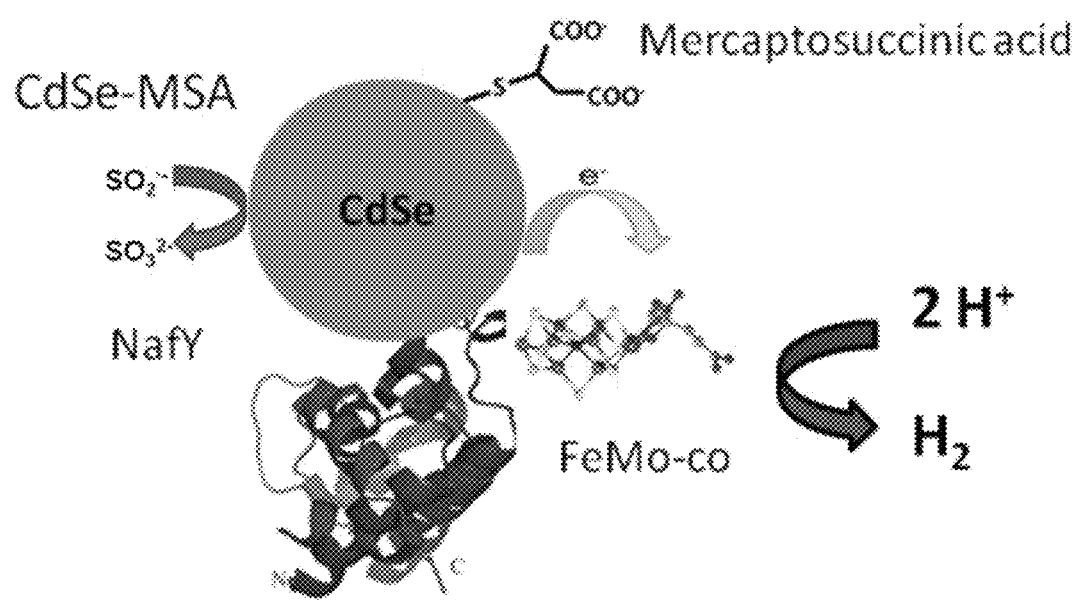
FIG. 11. Representation of a CdSe-MSA.NafY.FeMo-co System Illuminated with Visible Light. NafY.FeMo-co adsorbed on the surface of CdSe-MSA is photo-reduced and catalyzes the production of hydrogen from protons dissolved in solution.

The experiments presented above demonstrate that the CdSe-MSA would form a complex with the NafY protein. The EPR based characterization of the CdSe-MSA.NafY-.FeMo-co system showed that photo-reduction of FeMo-co upon illumination was likely. The CdSe-MSA had exhibited photo-reductive activity by its ability to reduce methyl viologen when illuminated with a 500 watt halogen lamp, detected by changes in UV-vis absorbance. All of these evidences supported the hypothesis that a CdSe-MSA.NafY.FeMo-co system when illuminated should perform a reduction of aqueous protons as schematically described in FIG. 11. Sodium dithionite (2 mM) would be added to the system for the dual purpose of 1) acting as a sacrificial electron donor to refill the electron hole after the generation of excitons in the CdSe upon illumination, and 2) acting as an oxygen scavenger to preserve the anaerobic environment for FeMo-co.

The hydrogen generation experiments were performed with the variable being the extent of excess of CdSe-MSA with respect to NafY.FeMo-co, ranging in ratios of 8:1, 4:1, 2:1, 1:1 and 0.5:1. The NafY.FeMo-co was prepared as previously described with all the NafY bound with FeMo-co in a 1:1 ratio. The CdSe-MSA and NafY.FeMo-co were initially mixed with a low concentration of sodium dithionite (0.2 mM) and allowed to mix for one minute to form a complex without interference from sodium dithionite. After the initial time for complex formation, additional sodium dithionite was added to a final concentration of 2.0 mM. All samples and controls were then positioned in front of the halogen lamp.

The head space gas of experimental and control samples were analyzed at multiple time points by gas chromatography. Samples from control reactions of CdSe-MSA, NafY.FeMo-co and CdSe-MSA.FeMo-co showed no signs of hydrogen throughout. Interestingly, no hydrogen was initially detected, but hydrogen was detected after 24 hours of illumination from the reaction with 1:1 ratio of CdSe-MSA to NafY.FeMo-co. The other comparable reactions with other ratios of CdSe-MSA.NafY.FeMo-co showed no signs of hydrogen generation. The experiment was repeated and still only the 1:1 samples showed hydrogen production. All total there were four different repetitions of the reaction with 1:1 CdSe-MSA.NafY.FeMo-co that generated hydrogen starting at 24 to 30 hours and continuing to produce hydrogen until at least 114 hours (FIG. 12A).

Figure 12B:
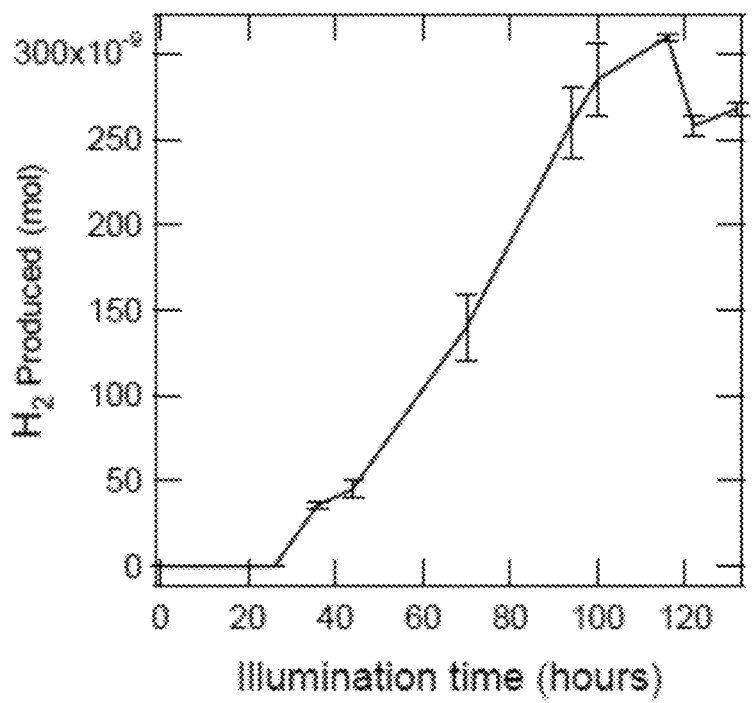

Two of the 1:1 samples were duplicates with samples analyzed at the same time and the data are shown in FIG. 12B with error bars to demonstrate reasonable consistency.

The generation of hydrogen continued to between 100 to 114 hours. The maximum amount detected at that point was 316 nmols of hydrogen produced over a period of 64 hours. With respect to the amount of FeMo-co used in the reaction, 105 nmol $H_2$ was produced per nanomole of FeMo-co. Stated as a specific rate, 1.8 nmol $H_2$/nmol FeMo-co/hour was the rate of hydrogen production.

The hydrogen generation experiments were also attempted with MoFe protein in 100 mM MOPS, 1 mM dithionite, pH of 7.0 with added CdSs-MSA. Previously, a report [7], has shown the evolution of hydrogen from MoFe protein with Ru(bypy)$_2$ attached.

As in the experiment above with the CdSe-MSA.NafY.FeMo-co, reactions with CdSe-MSA and the MoFe protein in varying ratios were set up. Control samples were CdSe-MSA (720 nM) and MoFe protein (360 nM). Head gas samples (100 μL) were analyzed by gas chromatography.

Initially, precipitation was observed with the higher ratios of CdSe-MSA to MoFe protein within the first 30 minutes of illumination. The 2 to 1 sample remained soluble and translucent for three hours but became cloudy thereafter. Solubility experiments were performed with different pH buffered solutions of 7.0 to 8.0. The conditions with pH of 7.8 and 8.0 showed better solubility with the CdSe-MSA.MoFe protein system as compared to the lower pH values. No notable hydrogen production was observed with these set of samples.

An additional reaction was performed with CdSe-TOP and FeMo-co. Given the high photo-activity of the CdSe-TOP, a sample in chloroform was combined with FeMo-co dissolved in NMF solution with all solutions and samples thoroughly degassed. The reaction was performed in a quartz cuvette with 5.0 μM CdSe-TOP and 1.25 μM FeMo-co. The headspace was analyzed after one hour of illumination and determined to contain 28 nmol of hydrogen. This reaction was performed lacking controls and needs to be re-performed in a proper experimental context with appropriate controls and variables. Although this result needs to be further investigated, the result is noteworthy due to its relative high activity. This system should be investigated further with duplicates, concentration dependencies and control samples to corroborate this result.

4. Discussion

Toward the goal of producing hydrogen passively as an alternative fuel, a novel advanced material has been developed. CdSe nanoparticles complexed with FeMo-co, in both aqueous and organic solvent systems were illuminated with visible light and evolved hydrogen. The CdSe-MSA.NafY.FeMo-co system when illuminated evolved hydrogen consistently in four different experimental sets under the same reaction conditions. The CdSe-TOP.FeMo-co system produced hydrogen in one sample, but awaits optimization. While not wishing to be bound by theory, the rationale behind the experiments was as follows. CdSe nanoparticles with bandgap energy of 1.7 eV are able to absorb incident light in the visible range, and create an electron-hole pair. CdSe nanoparticles were selected because their band gap energy is a close match to the thermodynamic potential of the $H^+/H_2$ couple. With the addition of NafY.FeMo-co to the CdSe nanoparticles, a complex was formed and thus put the NafY.FeMo-co in close enough proximity so that the exciton participates in electron transfer to the NafY.FeMo-co. This photo-induced reduction of FeMo-co then in turn catalyzed the reduction of protons in the aqueous solution to form hydrogen.

4.1 Efficacy of Hydrogen Generation from CdSe.FeMo-co Systems

There were some important discoveries along the way that contributed to the success of assembling a complex that when exposed to high intensity light would result in hydrogen evolution. Utilization of CdSe-TOP and the CdSe-MSA nanoparticles with sizes that matched the bandgap energy associated with the thermodynamic potential of the $H^+/H_2$ couple and the adsorbed FeMo-co's reduction potential to facilitate its photo-reduction was crucial. CdSe nanoparticle sizes in the range of 2.4 to 2.7 nm in diameter appeared to be suitable for complex formation, monitored by fluorescence emission quenching and EPR. Particles of this size also were suitable for hydrogen experiments.

Electron transfer between the excited CdSe nanoparticles and the adsorbed FeMo-co species was necessary to reduce FeMo-co. For this to occur, a complex had to form between CdSe and FeMo-co. This was demonstrated both in the organic CdSe-TOP.FeMo-co system and the aqueous CdSe-MSA.NafY.FeMo-co system by fluorescence emission quenching. To obtain evidence that in both complexed systems FeMo-co would be photo-reduced, samples were interrogated by EPR spectroscopy. The EPR spectrum with the CdSe-TOP.FeMo-co system indicated that the population of the resting state S=3/2 spin state was largely diminished. A new signal was observed at g =1.98 and 1.97. This observed S=1/2 spin state suggested a change in electronic spin state, possibly due to reduction of the S=3/2 spin state of FeMo-co.

The EPR spectra of the CdSe-MSA.NafY.FeMo-co system showed a similar S=3/2 spin state with a sharpened line shape consistent with an additional ligand (NafY) on FeMo-co. The complexed system spectrum was similar to the NafY.FeMo-co control sample indicating that the interaction between CdSe-TOP and FeMo-co had not perturbed the FeMo-co electronic structure. FeMo-co had survived the complex formation process and would be suitable for photo-reduction.

When the effect of light on this same CdSe-MSA.NafY.FeMo-co sample was examined, the EPR spectrum showed a significant change in the S=3/2 spin state of FeMo-co compared to the previous EPR spectrum. The post illuminated sample showed a largely diminished EPR species with the same line shape as the S=3/2 spin state prior to illumination. The diminished signal intensity corresponds to a change in the population of the S=3/2 spin state suggesting that illumination had initiated an electron transfer from CdSe-MSA to the adsorbed NafY.FeMo-co.

The most successful system of the aqueous and organic systems with repeatable results for hydrogen generation was a one to one CdSe-MSA.NafY.FeMo-co system. The maximum hydrogen production was 316 nanomoles or 105 nanomoles $H_2$/nanomoles NafY.FeMo-co. There was one CdSe-TOP.FeMo-co sample which was illuminated and produced 28 nanomoles of hydrogen in one hour; 22.4 nanomoles $H_2$/nanomoles FeMo-co. The experiment with the CdSe-TOP.FeMo-co sample needs to be re-performed in a proper experimental context with appropriate controls and variables.

There were other considerations that are beneficial for analyzing the study. The interaction between the CdSe nanoparticles and the FeMo-co was different in the organic versus aqueous systems. The CdSe-TOP and the FeMo-co formed a complex in a direct interaction between the two. This resulted in an EPR signal at g=1.99 resulting in an S=1/2 spin state sub-manifold signal. Coordination of Fe in FeMo-co to the selenium of the nanoparticle may have produced this change in electronic structure of the FeMo-co [39].

In the aqueous system, the CdSe-MSA forms a complex with the NafY protein. Because of the size of NafY being approximately 15 nanometers in diameter and the FeMo-co bound to the NafY being 8 to 10 angstroms (0.8 to 1.0 nm), this resulted in FeMo-co being close enough for electron transfer without being directly complexed with the nanoparticle. This was shown in the EPR spectrum of the CdSe-MSA.NafY.FeMo-co system when first combined. There was little change in the EPR signal at g=(4.41, 3.71 and 2.03) representing the S=3/2 spin state; however, when this sample was illuminated with intense visible light, the EPR signal intensity was largely diminished indicating a change in the population of S=3/2 spin states to some corresponding EPR silent state. An EPR silent signal is indicative of a diminished concentration of unpaired spins [55]. This change was interpreted to mean that electron transfer had occurred between the excited CdSe-MSA to the FeMo-co inside NafY.

A few other factors to consider in the analysis of what led to the hydrogen evolution are as follows. There is a distinct advantage of the aqueous based CdSe-MSA.NafY.FeMo-co system because of the ready source of protons as opposed to the chloroform dissolved CdSe-TOP.FeMo-co. The samples were set 8 centimeters from the 500 watt halogen lamp, which promoted catalysis. Temperature maintenance was important in order to prevent degradation of the NafY protein conjugated to FeMo-co, 30±2° C. FeMo-co itself is not as temperature sensitive as the protein.

4.2 Possible Explanation for the Observed Lag of the CdSe-MSA.NafY.FeMo-co System for Hydrogen Generation One observed phenomenon in the hydrogen generation experiments using the CdSe-MSA.NafY.FeMo-co system was interesting. The system did not show detectable hydrogen until about 24 hours after the initiation of illumination. The most plausible explanation for the observed lag could be that there were pH effects from dithionite reacting with water according to equations 2 and 3 [56]. Over time the pH would decrease and more protons would be available for reduction, especially as the equilibrium shifted right as shown in equation 2. The sodium dithionite is in excess in the reaction vessel. To explain the eventual cessation of hydrogen production, once the dithionite was depleted then the hydrogen production levels off because protons are less available. An experiment interrogating the effects of pH on hydrogen production either by direct changes in the pH of the buffered solution and/or changes in sodium dithionite concentration would be beneficial towards probing this issue.

$$S_2O_4^{2-} \leftrightarrows 2SO_2^- \quad (\text{Eq. 2})$$

$$SO_2^- + H_2O \leftrightarrows HSO_3^- + H^+ + e^- \quad (\text{Eq. 3})$$

The reaction in equation 2 is shown as an equilibrium between the dimer and monomer forms of dithionite. It has been shown that the real electron donating species is the radical monomer, $SO_2^-$ [59]. As stated previously, the dithionite serves as an electron donor to fill holes generated in the valence band with CdSe exciton formation. The second purpose of dithionite is to serve as an oxygen scavenger to preserve anaerobicity in the reaction vessel. An additional purpose may be to indirectly supply protons for reduction. So reaction conditions that would favor the formation of the radical monomer species and thereby increase the H+ concentration as it reacted with water would facilitate the overall reaction of hydrogen generation.

The experimental setup required a cooling method to maintain a temperature of 30° C. to prevent degradation of the NafY protein in the reaction vessel. This required the use of a Peltier cooling device because the halogen lamp used readily heated the test reaction vessel contents to 55° C. and above. Reaching a stable temperature in the reaction vessel may have taken a number of hours. Higher temperatures, tested in the range of 2 to 40° C., have shown a tendency to shift the dithionite equilibrium to the monomer side [59]. The NafY protein did prove to be more robust than our expectations. Experiments could be designed to find the maximum hydrogen generation corresponding to a higher temperature. Exploration of pH effects and increased concentrations of dithionite could also enhance the monomer side of the equilibrium reaction and merit investigation [59].

Other variables that could be explored to reduce the lag time could be increasing the intensity of the light and varying the concentrations of the reactants. The explanation for the lag in $H_2$ production deserves further experimentation with the proper controls and variables.

4.3 Comparison of this Hydrogen Production Method with Other Published Methods

The generation of hydrogen from a sophisticated bioconjugate material such as CdSe-MSA.NafY.FeMo-co is significant. To gauge how significant, the effectiveness of the system presented as part of the current study is compared to other published bioconjugate hydrogen generation methods (Table 2). The amount of hydrogen or hydrocarbon production and the rates for the hydrogen formation have been recalculated for direct comparisons. The first method combines CdSe nanoparticles with hydrogenase at a pH of 4.75 with ascorbic acid being the electron donor that produced hydrogen at an impressive rate (93 nmol $H_2$/nmol active material/min). However, the reaction was only able to produce hydrogen at this rate for five minutes, possibly due to degradation of the protein with the acidic conditions [5]. The second method involved several MoFe proteins variants that allowed for conjugation of a Ru(bypy)$_2$ photosensitizer to one of three substituted cysteines near the bound FeMo-co. The system was able to produce 1.9 nmol $H_2$/nmol active material/min. The electron donor used was 200 mM dithionite and it was necessary that this excess be used to sustain the reaction for 50 minutes, which diminished in production after that point [7].

TABLE 2

Analytical Comparison of Different Hydrogen Production Systems

| Method | *Rate of Production ($H_2$/nmol active material/minute) | Maximum (nmol) | Time (min) | Ref. No. | Reaction Conditions |
|---|---|---|---|---|---|
| CdTe/Hydrogenase | 93 | 70 | 5 | 5 | pH 4.75 |
| Ru(bypy)$_2$/MoFe protein | 1.9 | 2300 | 50 | 7 | 200 mM Na$_2$S$_2$O$_4$ |
| **Eu$^{II}$-DTPA/FeMo-co | 0.097 | 5.8 | 60 | 57 | |
| CdSe-MSA-NafY-FeMo-co | 0.030 | 316 | 6840 | this study | pH 8.0; 2.0 mM Na$_2$S$_2$O$_4$ |

*Rates of production have been restated in equivalent units for comparison purposes.
**Ethylene production measured Another method of not hydrogen production, but hydrocarbons production, is included since it uses FeMo-co.

FeMo-co was combined with cyanide ion and europium (II) diethylenetriaminepentaacetate [Eu$^{II}$-DTPA], a strong photoactivated reductant. Hydrocarbons were produced with this system and more particularly ethane at 0.097/nmol H$_2$/nmol active material/min. The reaction was also attempted with carbon monoxide, but the hydrocarbons produced were considerably less. FeMo-co typically hydrolyzes in aqueous solvents, however, in this report it showed 85% activity after the first hour of being in an aqueous based solvent [57]. As seen in Table 2, the effectiveness of the CdSe-MSA.NafY.FeMo-co system for hydrogen formation is comparable with the other reported systems. In terms of the rate of production, this system requires improvement to be competitive. However, this system is competitive enough, so that efforts expended towards increasing the amount produced and the rate of production are worthwhile. In terms of stability, the CdSe-MSA.NafY.FeMo-co system may have an advantage in that it was operational for 90 plus hours versus five minutes or one hour or four hours as with the other published systems. The length of time that the system is catalytically active could be a real plus as long as optimization of the system could increase the rate of hydrogen production.

4.4 Potential Improvements for the CdSe.FeMo-co Systems

Ways to enhance the hydrogen production using the CdSe-MSA.NafY.FeMo-co system include the following. The current systems were examined at a pH of 8.0. In the aqueous CdSe-MSA.NafY.FeMo-co system, a feasible experiment would be to probe the limits of pH with respect to hydrogen production, the stability of the system, and maintaining the solubility of the system. At lower pH values, the higher concentration of protons as substrates will drive the equilibrium forward. The method using CdTe-hydrogenase discussed earlier utilized a pH of 4.75 [5]. Impressive hydrogen production was observed, but only for five minutes. pH also plays a role in maintaining solubility with the CdSe-MSA. If the mercaptosuccinic acid is protonated, the result may be that the nanoparticles lose their ability to be aqueously solubilized. The pK$_a$s of the carboxylic acid functional groups in mercaptosuccinic acid are pK$_{a1}$ of 3.64 and pK$_{a2}$ of 4.64. Consequently, any buffered solution in the pH range of 7.0 to 8.0 used to form the complex should maintain solubility. As seen with CdSe-MSA.MoFe protein experiments, pH lower than 7.8 decreased the solubility of the system. There could have been more non-specific binding between the MoFe protein and the nanoparticle that could have contributed to diminished solubility. A study comparing solubility of the system compared to the protein with the FeMo-co (MoFe protein versus NafY protein), complexed to the CdSe-MSA would be beneficial to determine the size of the protein and its effects on solubility.

As mentioned earlier, the effects of decreasing pH from the presence of sodium dithionite and its hydrolysis could be a variable pertaining to the molar volume of hydrogen produced. The effects of different sodium dithionite concentrations could be investigated. With an increase in the sodium dithionite, it will be important to combine the CdSe-MSA and NafY.FeMo-co at a lower concentration (0.2 sodium dithionite) as was done previously. This will give the complex adequate time to avoid competing effects from the dithionite for positions on the CdSe-MSA surface. A validation that higher dithionite concentration may increase the amount of hydrogen produced is found in the report that utilized the MoFe protein with bound Ru(bypy)$_2$. In that study, higher dithionite concentration, in a range from 20 mM to 200 mM, resulted in greater amounts of evolved hydrogen corresponding to increased dithionite [7]. The reaction with 200 mM dithionite produced a fivefold higher amount of hydrogen produced compared to the 20 mM dithionite sample. Another consideration regarding the dithionite is the temperature dependent equilibrium favoring the monomer form of dithionite which is the reducing species [59]. The system was more robust than anticipated and could possibly withstand higher temperatures.

There are other experimental conditions or variables that could be investigated in order to optimize hydrogen production. A different kind of nanoparticle could be synthesized and used as in the previous experiments such as cadmium telluride (CdTe). The bandgap energy of CdTe may be a closer match for the H$_2$/H$^+$ thermodynamic couple and FeMo-co's reduction potential. A study with various size of the same kind of nanoparticle could be conducted in order to ascertain any size dependent results for hydrogen production. Other variables to explore in the hydrogen generation experiments would be the kind of lamp used for illumination and temperature effects on the hydrogen generation.

An interesting issue is the source of protons with the organic CdSe-TOP.FeMo-co system in chloroform. The 1 mM dithionite, 25 mM Tris solution in NMF solution with FeMo-co is the source of protons. With the addition of 5 μL of FeMo-co in NMF, 1 mM dithionite this equates to introducing 100 nanoliters of water to the sample. The one cuvette sample saw the production of 28 nmols of hydrogen in one hour. How best to increase the source of protons in this system warrants further experimentation. The addition of pentafluorothiophenol (C$_6$F$_5$S$^-$) to FeMo-co was suggested as a source of protons catalytically, not as an ultimate source [57]. The C$_6$F$_5$S$^-$ replaces one of the amide ligands of the solvent NMF solution. Although the use of this ligand was inadequately explored in the study referenced, it does deserve investigation.

5. Conclusion

This study described complexes formed between CdSe and FeMo-co in organic and in aqueous solvents and the experiments probing their interactions, along with their capability to produce dihydrogen when illuminated. While the experimental system studied here requires further optimization, it contributes to the pursuit of developing sustainable energy sources.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While specific embodiments of the subject disclosure have been discussed, the above specification is illustrative and not restrictive. Many variations of the disclosure will become apparent to those skilled in the art upon review of this specification. The full scope of the invention should be determined by reference to the claims, along with their full scope of equivalents, and the specification, along with such variations.

INCORPORATION BY REFERENCE

All publications, patents and patent applications cited above are incorporated by reference herein in their entirety for all purposes to the same extent as if each individual publication or patent application were specifically indicated to be so incorporated by reference.

REFERENCES

[1] International Energy Agency. Deploying renewables: principles for effective policies. Paris: International Energy Agency, 2008.

[2] Service R F. Chemistry: artificial leaf turns sunlight into a cheap energy source. Science 2011; 332: 25.

[3] Kudo A, Miseki Y. Heterogeneous photocatalyst materials for water spitting. Chem Soc Rev 2009; 38; 253-78.

[4] Tvrdy K., Kamat P. V. Substrate driven photochemistry of CdSe quantum dot films: charge injection and irreversible transformations on oxide surfaces. J Phys Chem A 2009; 113; 3765-72.

[5] Brown K A, Dayal S, Ai X, Rumbles G, King P W. Controlled assembly of hydrogenase-CdTe nanocrystal hybrids for solar hydrogen production. J Am Chem Soc 2010; 132, 9672-80.

[6] Reisner E, Powell D J, Cavazza C, Fontecilla-Camps J C, Armstrong F A. Visible light-driven $H_2$ production by hydrogenases attached to dye-sensitized $TiO_2$ nanoparticles. J Am Chem Soc 2009; 131; 18457-66.

[7] Roth L E, Nguyen J C, Tezcan F A. ATP-and iron-protein-independent activation of nitrogenase catalysis by light. J Am Chem Soc 2010; 132, 13672-4.

[8] Rees D C, Tezcan A F, Haynes C A, Walton M Y, Andrade S, Einsle O, Howard J B. Structural basis of biological nitrogen fixation. Philos Transact A Math Phys Eng Sci 2005; 363; 971-84.

[9] Lancaster K M, Roemelt M, Ettenhuber P, Hu Y L, Ribbe M W, Neese F, et al. X-ray emission spectroscopy evidence a central carbon in the nitrogenase iron-molybdenum cofactor. Science 2011; 334; 974-7.

[10] Seefeldt L C, Hoffman B M, Dean D R. Mechanism of Mo-dependent nitrogenase. Annu Rev Biochem 2009; 78; 701-22.

[11] Igarashi R Y, Seefeldt L C. Nitrogen fixation: the mechanism of the Mo-dependent nitrogenase. Crit Rev Biochem Mol Biol 2003; 38; 351-84.

[12] Seefeldt L C, Rasche M E, Ensign S A. Carbonyl sulfide and carbon dioxide as new substrates, and carbon disulfide as a new inhibitor, of nitrogenase. Biochemistry 1995; 34; 5382-9.

[13] Sakurai H, Masaukawa H. Promoting R and D in photobiological hydrogen production utilizing mariculture-raised cyanobacteria. Marine Biotechnol 2007; 9; 128-45.

[14] Matylitsky V V, Dworak L, Breus V V, Basche T, Wachtveitl J. Ultrafast chargeseparation in multiexcited CdSe quantum dots mediated by adsorbed electron acceptors. J Am Chem Soc 2009; 131; 2424-5.

[15] Burgess B K, Stiefel E I, Newton W E. Oxidation-reduction properties and complexation reactions of the iron-molybdenum coafactor of nitrogenase. J Biol Chem 1980; 255; 353-6.

[16] Watanabe T, Honda K. Measurement of the extinction coefficient of the methyl viologen cation radical and the efficiency of its formation by semiconductor photocatlysis. J Phys Chem 1982; 86; 2617-9.

[17] Mahler B, Spinicelli P, Buil S, Quelin X, Hermier J P, Dubertret B. Towards non-blinking colloidal quantum dots. Nat Mater 2008; 7; 659-64.

[18] Mohamed M B, Tonti D, Al-Salman A, Chemseddine A, Chergui M. Synthesis of high quality zinc blende CdSe nanocrystals J Phys Chem B 2005; 109; 10533-7.

[19] Peng X G, Wickham J, Alivisatos A P. Kinetics of II-IV and III-IV colloidal semiconductor nanocrystal growth: focusing of size distributions. J Am Chem Soc 1998; 120; 5343-4.

[20] Yu W W, Qu L H, Guo, W Z, Peng X G. Experimental determination of the extinction coefficient of CdTe, CdSe, and CdS nanocrystals. Chem Mater 2003; 15; 2854-60.

[21] Christiansen J, Goodwin P J, Lanzilotta W N, Seefeldt L C, Dean, D R. Catalytic and biophysical properties of a nitrogenase Apo-MoFe protein produced by a nifB-deletion mutant of *Azotobacter vinelandii*. Biochemistry 1998; 37; 12611-23.

[22] Laemmli, U K. Cleavage of structureal proteins during assembly of head of bacteriophage-T4. Nature 1970; 227, 680.

[23] Lowry O H, Rosebrough N J, Farr A L, Randall R J. Protein measurement with the Folin phenol reagent. J Biol Chem 1951; 193; 265-75.

[24] Shah V K, Brill W J. Isolation of an iron-molybdenum cofactor from nitrogenase. Proc Natl Acad Sci USA 1977; 74; 3249-53.

[25] Van de Bogart M, Beinert, H. Micro methods for the quantitative determination of iron and copper in biological material. Anal Biochem 1967; 20; 325-34.

[26] Burgess B K. The iron molybdenum cofactor of nitrogenase. Chem Rev 1990; 90; 1377-1406.

[27] Rubio L M, Singer S W, Ludden P W. Purification and characterization of NafY (apodinitro-genase gamma subunit) from *Azotobacter vinelandii*. J Biol Chem 2004; 279; 19739-46.

[28] Smith P K, Krohn R I, Hermanson G T, Mallia A K, Gartner, F H, Provenzano, M D, et al. Measurement of protein using bicinchoninic acid. Anal Biochem 1985; 150; 76-85.

[29] Callan J F, Mulrooney R C, Kamila S. Luminescent detection of ATP in aqueous solution using positively charged CdSe-ZnS quantum dots. J Fluoresc 2008; 18; 1157-61.

[30] Kong C, Qin L X, Liu J F, Zhong X H, Zhu L Y, Long Y T. Determination of dissolved oxygen based on photoinduced electron transfer from quantum dots to methyl viologen. Analyt Meth 2010; 2; 1056-62.

[31] George S J, Igarashi R Y, Xiao Y, Hernandez J A, Demuez M, Zhao D, et al. Extended X-ray absorption fine structure and nuclear resonance vibrational spectroscopy reveal that NifB-co, a FeMo-co precursor, comprises a 6Fe core with interstitial light atom. J Am Chem Soc 2008; 130; 5673-80.

[32] Seefeldt L C, Morgan T V, Dean D R, Mortenson L E. Mapping the site(s) of MgATP and MgADP interaction with the nitrogenase of *Azotobacter vinelandii*. J Biol Chem 1992; 267; 6680-8.

[33] Murray, C B, Norris, D J, Bawendi M G. Synthesis and characterization of nearly mono-disperse CdE (E=S, Se, Te) semiconductor nanocrystallites. J Am Chem Soc 1993; 115; 8706-15.

[35] Nozik, A J. Nanoscience and nanostructures for photovoltaics and solar fuels. Nano Lett 2010; 10; 2735-41.

[36] Biju V, Itoh T, Anas A, Sujith A, Ishikawa M. Semiconductor quantum dots and metal nanoparticles: syntheses, optical properties, and biological applications. Anal Bioanal Chem 2008; 391; 2469-95.

[37] Kamat P V. Quantum dot solar cells; semiconductor nanocrystals as light harvesters. J Phys Chem C 2008; 112; 18737-53.

[38] Landes C, Burda C, Braun M, EI-Sayed M A. Photoluminescence of CdSe nanoparticles in the presence of a hole acceptor: n-butylamine. J Phys Chem B 2001; 105; 2981-6.

[39] Hagen W R. EPR spectroscopy as a probe of metal centres in biological systems. Dalton Trans 2006; 4415-34.

[40] Frank P, Angove H C, Burgess B K, Hodgson, K O. Determination of ligand binding constants for the iron-molybdenum cofactor of nitrogenase: monomers, multimers, and cooperative behavior. J Biol Inorg Chem 2001; 6; 683-97.

[41] Barney B M, McClead J, Lukoyanov D, Laryukhin M, Yang T C, Dean D R, et al. Diazene (HN=NH) is a substrate for nitrogenase: insights into the pathway of $N_2$ reduction. Biochemistry 2007; 46; 6784-94.

[42] Smith B E, Durrant M C, Fairhurst S A, Gormal C A, Gronberg K L C, Henderson R A, et al. Exploring the reactivity of the isolated iron-molybdenum cofactor of nitorgenase. Coord Chem Rev 1999; 185-6; 669-87.

[43] Barney B M, Lee H I, Dos Santos P C, Hoffman B M, Dean D R, Seefeldt L C. Breaking the $N_2$ triple bond: insights into the nitrogenase mechanism. Dalton Trans 2006; 2277-84.

[44] Igarashi R Y, Laryukhin M, Dos Santos P C, Lee H I, Dean D R, Seefeldt L C, Hoffman B M. Trapping H-bound to the nitrogenase FeMo-cofactor active site during $H_2$ evolution: characterization by ENDOR spectroscopy. J Am Chem Soc 2005; 127; 6231-41.

[45] Wuister S F, Swart I, van Driel F, Hickey S G, Donega CD. Highly luminescent water-soluble CdTe quantum dots. Nano Lett 2003; 3, 503-7.

[46] Winter J O, Gomez N, Gatzert S, Schmidt C E, Korgel B A. Variation of cadmium sulfide nanoparticle size and photoluminescence intensity with altered aqueous synthesis conditions. Colloids Surfs A; 2005; 254; 147-57.

[47] Zhou C, Shen H, Guo Y, Xu L, Niu J, Zhang Z, et al. A versatile method for the preparation of water-soluble amphiphilic oligomer-coated semiconductor quantum dots with high fluorescence and stability. J Colloid Interface Sci 2010; 344; 279-85.

[48] Kloepfer J A, Bradforth S E, Nadeau J L. Photophysical properties of biologically compatible CdSe quantum dot strucutures. J Phys Chem B 2005; 109; 9996-10003.

[49] Zhelev Z, Bakalova R, Ohba H, Jose R, Imai Y, Baba Y. Uncoated broad fluorescent and size-homogeneous CdSe quantum dots for bioanalyses. Anal Chem 2006; 78; 321-30.

[50] Han H Y, Sheng Z H, Liang H G. A novel method for the preparation of water-soluble and small size CdSe quantum dots. Mater Lett 2006; 60; 3782-5.

[51] Noh M, Kim T, Lee H, Kim C K, Joo S W, Lee K. Fluorescence quenching caused by aggregation of water-soluble CdSe quantum dots. Colloids Surfs A 2010; 359; 39-44.

[52] Rogach A L, Kornowski A, Gao M Y, Eychmuller A, Weller H. Synthesis and characterization of a size series of extremely small thiol-stabalized CdSe nanocrystals. J Phys Chem B 1999; 103; 3065-9.

[53] Dyer D H, Rubio L M, Thoden J B, Holden H M, Ludden P W, Rayment I. The three-dimensional structure of the core domain of Naf Y from *Azotobacter vinelandii* determined at 1.8 Å resolution. J Biol Chem 2003; 278; 32150-6.

[54] Mehta S K, Chaudhary S, Kumar S, Singh S. Facile synthesis, growth mechanism, and optical properties of CdSe nanoparticles in self-assembled micellar media and their efficient conjugation with proteins. J Nanopart Res 2010; 12; 697-1709.

[55] Pickett C J, Vincent K A, Ibrahim S K, Gormal S C, Smith B E, Best S P. Electron-transfer chemistry of the iron-molybdenum cofactor of nitrogenase: delocalized and localized reduced states of FeMoco which allow binding of carbon monoxide to iron and molybdenum. Chem Eur J 2003; 9; 76-87.

[56] Deistung J, Cannon F C, Cannon M C, Hill S, Thorneley R N. Electron transfer to nitrogenase in *Kiebsilla pneumoniae;* nifF gene cloned and the gene product, a flavodoxin, purified. Biochem J 1985; 231, 743-753.

[57] Lee C C, Hu Y, Ribbe M W. ATP-independent formation of hydrocarbons catalyzed by isolated nitrogenase cofactors. Angew Chem Int Ed Engl 2012; 51; 1947-9.

[58] Le Gall T, Ibrahim S K, Gormal C A, Smith B E, Pickett C J. The isolated iron-molybdenum cofactor of nitrogenase binds carbon monoxide upon electrochemically accessing reduced states. Chem Comm 1999; 773-4.

[59] Mayhew, S. G. The redox potential of dithionite and SO-2 from equilibrium reactions with flavodoxins, methyl viologen and hydrogen plus hydrogenase. Eur J Biochem 1978; 85, 535-547.

[60] Curatti, L., Hernandez, J. A., Igarashi, R. Y., Soboh, B., Zhao, D., and Rubio, L. M. (2007) In vitro synthesis of the iron-molybdenum cofactor of nitrogenase from iron, sulfur, molybdenum, and homocitrate using purified proteins, *Proc Natl Acad Sci USA* 104, 17626-17631.

[61] Rubio, L. M., Singer, S. W., and Ludden, P. W. (2004) Purification and characterization of NafY (apodinitrogenase gamma subunit) from *Azotobacter vinelandii, J Biol Chem* 279, 19739-19746.

[62] Hernandez, J. A., Phillips, A. H., Erbil, W. K., Zhao, D., Demuez, M., Zeymer, C., Pelton, J. G., Wemmer, D. E., and Rubio, L. M. (2011) A sterile alpha-motif domain in NafY targets apo-NifDK for iron-molybdenum cofactor delivery via a tethered domain, *J Biol Chem* 286, 6321-6328.

[63] Matylitsky V V, Dworak L, Breus V V, Basche T, Wachtveitl J. Ultrafast charge separation in multiexcited CdSe quantum dots mediated by adsorbed electron acceptors. *J Am ChemSoc,* 2009; 131; 2424-5.

[64] Thorneley, R. N.; Lowe, D. J. The mechanism of Klebsiella pneumonia nitrogenase action. Pre-steady-state kinetics of an enzyme-bound intermediate in $N_2$ reduction of $NH_3$ formation. *Biochemical Journal,* 1984, 224: 887-894.

[65] Lukoyanov, Dmitriy; Dikanov, Sergei A.; Yang, Zhi-Young; Barney, Brett M.; Samoilov, Rimma I.; Narasimhulu, Kuppala V.; Dean, Dennis R.; Seefeldt, Lance C.; Hoffman, Brian M. ENDOR/HYSCORE studies of the common intermediate trapped during nitrogenase reduction of $H_2H_2$, $CH_3N_2H$, and $N_2H_4$ support an alternativng reaction pathway for $N_2$ reduction. *J Am Chem Soc,* 2011, 133: 11655-11664.

[66] Igarashi, Robert I.; Laryukhin, Mikhail; Dos Santos, Patricia C.; Lee, Hong-In; Dean, Dennis R.; Seefeldt, Lance C.; Hoffman, Brian M. Trapping H-bound to the nitrogenase FeMo-cofactor active site during H2 evolution; characterization by ENOR spectroscopy. *J Am Chem Soc,* 2005, 127, 6231-6241.

[67] Sakurai H, Masaukawa H. Promoting R and D in photobiological hydrogen production utilizing mariculture-raised cyanobacteria. *Marine Biotechnol.* 2007; 9; 128-45.

[68] Winkler, Martin; Kawelke, Steffen; Happe, Thomas. Light driven hydrogen production in protein based semi-artificial systems. Bioresource Technology, 2011, 102: 8493-8500.

What is claimed is:

1. A method for preparing a system for photocatalytically producing hydrogen gas, comprising:
    (a) providing a water soluble cadmium selenide nanoparticle (CdSe) surface capped with mercaptosuccinate (CdSe-MSA);
    (b) providing an apodinitrogenase γ (NafY).FeMo-co complex comprising a NafY protein and an iron-molybdenum cofactor (FeMo-co); and
    (c) mixing the CdSe-MSA and the NafY.FeMo-co complex under anaerobic conditions to form a CdSe-MSA.NafY.FeMo-co system, wherein when illuminated with a visible light source, the CdSe-MSA.NafY.FeMo-co system is capable of photocatalytically producing hydrogen gas.

2. The method of claim 1, wherein step (a) further comprises exchanging surface capping agent from trioctylphosphine (TOP) in a CdSe-TOP nanoparticle to mercaptosuccinate, to form the CdSe-MSA.

3. The method of claim 2, wherein the CdSe-TOP nanoparticle has a diameter of about 2.4 nm to about 2.7 nm and the CdSe-MSA has a diameter of about 2.6 nm.

4. The method of claim 2, wherein the exchanging step is performed in methanol under reflux in the presence of a base.

5. The method of claim 4, wherein the base is tetrabutylammonium hydroxide.

6. The method of claim 1, wherein in step (b), the NafY protein is derived from *Azotobacter vinelandii*.

7. The method of claim 1, wherein in step (b), the FeMo-co is derived from a molybdenum-iron protein (MoFe protein).

8. The method of claim 7, wherein the MoFe protein is derived from *Azotobacter vinelandii* strain DJ995.

9. The method of claim 1, wherein step (b) further comprises combining the NafY protein with stepwise aliquots of the FeMo-co to form the NafY.FeMo-co complex.

10. The method of claim 9, wherein the FeMo-co is provided in N-methylformamide (NMF) solution and added stepwise to the NafY protein so that NMF does not exceed about 3% (v/v).

11. The method of claim 1, wherein in step (c), the CdSe-MSA and the NafY.FeMo-co complex are provided at about 1:1 molar ratio.

12. The method of claim 1, wherein in step (c), the CdSe-MSA is provided in the presence of a dithionite salt.

13. The method of claim 12, wherein the dithionite salt is kept at a sufficiently low concentration so as to allow the CdSe-MSA and the NafY.FeMo-co complex to bind to each other.

14. The method of claim 13, further comprising increasing the dithionite salt concentration to facilitate hydrogen gas production by the CdSe-MSA.NafY.FeMo-co system.

15. A method for producing hydrogen gas, comprising illuminating a CdSe-MSA.NafY.FeMo-co system with a visible light source, wherein the system produces hydrogen gas for an extended period of at least 5 hours.

16. The method of claim 15, wherein the system produces hydrogen gas for at least 10 hours.

17. The method of claim 15, wherein the system produces hydrogen gas for at least 90 hours.

18. A system for photocatalytically producing hydrogen gas, comprising:
    a water soluble cadmium selenide nanoparticle (CdSe) surface capped with mercaptosuccinate (CdSe-MSA); and
    a NafY.FeMo-co complex comprising a NafY protein and an iron-molybdenum cofactor (FeMo-co).

19. The system of claim 18, wherein the CdSe-MSA and the NafY.FeMo-co complex are present in about 1:1 molar ratio.

20. The system of claim 18, wherein when illuminated with a visible light source, the system is capable of photocatalytically producing hydrogen gas for an extended period of at least 5 hours.

21. The system of claim 18, wherein the system produces hydrogen gas for at least 10 hours.

22. The system of claim 18, wherein the system produces hydrogen gas for at least 90 hours.

23. The system of claim 18, wherein the system is kept under anaerobic conditions.

* * * * *